United States Patent [19]

Spielvogel et al.

[11] Patent Number: 5,280,119
[45] Date of Patent: Jan. 18, 1994

[54] HETEROCYCLIC AMINE-BORANES, AND METHOD OF INHIBITING DNA TOPOISOMERASE ACTIVITY AND/OR COMBATTING INFLAMMATION, HYPERLIPIDEMIA, AND/OR NEOPLASIA USING AMINE-BORANE COMPOUNDS

[75] Inventors: Bernard F. Spielvogel, Raleigh; Anup Sood, Durham; Iris H. Hall, Carrboro, all of N.C.

[73] Assignee: Boron Biologicals, Inc., Raleigh, N.C.

[21] Appl. No.: 786,279

[22] Filed: Nov. 1, 1991

[51] Int. Cl.$^5$ .................. C07F 5/02; A61K 33/22; A61K 43/00
[52] U.S. Cl. ........................ 544/229; 546/13; 548/110; 548/405; 424/1.1
[58] Field of Search ............ 544/229; 546/13; 548/110, 405

[56] References Cited

U.S. PATENT DOCUMENTS

| | | | |
|---|---|---|---|
| 3,341,582 | 9/1967 | Stafiej et al. | 544/229 |
| 3,415,776 | 12/1968 | White | 546/13 |
| 4,312,989 | 1/1982 | Spielvogel et al. | 546/13 |
| 5,023,513 | 6/1991 | Spielvogel et al. | 546/13 |
| 5,116,980 | 5/1992 | Gabel | 544/229 |
| 5,143,907 | 9/1992 | Spielvogel et al. | 514/64 |

OTHER PUBLICATIONS

Hall et al., Chemical Abstracts, vol. 116, No. 143648 (1991) (Abstract for Biomed. Pharmacother. 45 p. 333, 1991).
Gyori et al., Chemical Abstracts, vol. 100, No. 60906 (1984).
Emri et al., Chemical Abstracts, vol. 100, No. 174884 (1984).
Gyoeri et al., Chemical Abstracts, vol. 89, No. 108910 (1978).
Hall et al., Biomedicine & Pharmacotherapy, vol. 45, pp. 333-341 (1991).

Primary Examiner—Emily Bernhardt
Attorney, Agent, or Firm—Steven J. Hultquist

[57] ABSTRACT

Heterocyclic amine-borane compounds of the formula:

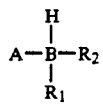

wherein:
A is a heterocyclic amine moiety selected from the group consisting of piperidine, substituted piperidine, piperazine, substituted piperazine, imidazole, substituted imidazole, pyrazole, substituted pyrazole, pyrazine, substituted pyrazine, pyrrole, substituted pyrrole, pyrrolidine, substituted pyrrolidine, indole, substituted indole, indoline, substituted indoline, quinoline, substituted quinoline, isoquinoline, substituted isoquinoline, thiazole, substituted thiazole, oxazole, substituted oxazole, thiazolidine, and substituted thiazolidine, wherein substitution is at any or all substituent positions, and comprises substituents selected from the group consisting of alkyl (preferably $C_1$-$C_{10}$ linear or branched alkyl), alkylaryl, aryl, aralkyl, nitro, alkoxy, hydroxy, cyano, thiol, and halo;
$R_1$ is selected from H, alkyl (preferably $C_1$-$C_{10}$ linear or branched alkyl), alkylaryl, aryl, and arylalkyl; and
$R_2$ is selected from CN, COOH, COOR$_3$, and CONHR$_3$ where R$_3$ is selected from H, alkyl (preferably $C_1$-$C_{10}$ linear or branched alkyl), alkylaryl, aryl, aralkyl.

The heterocyclic amine-borane compounds of the invention are bioactive in character, variously exhibiting anti-tumor, anti-inflammatory, and anti-hyperlipidemic activity. In another aspect, the invention relates to a method of inhibiting enzyme activity (e.g., DNA topoisomerase II, PRPP amidotransferase, IMP dehydrogenase, dihydrofolate reductase, and/or ribonucleotide reductase) in an in vitro or in vivo system, comprising administering to the system an enzyme-inhibitingly effective amount of a Lewis-base borane adduct, such as for example a heterocyclic amine-borane compound of the foregoing formula.

8 Claims, No Drawings

HETEROCYCLIC AMINE-BORANES, AND METHOD OF INHIBITING DNA TOPOISOMERASE ACTIVITY AND/OR COMBATTING INFLAMMATION, HYPERLIPIDEMIA, AND/OR NEOPLASIA USING AMINE-BORANE COMPOUNDS

BACKGROUND OF THE INVENTION

1. Field of the Invention

The present invention relates to amine-borane compounds, including novel heterocyclic amine-boranes, and to a method of inhibiting enzyme (e.g., DNA topoisomerase) activity and/or combatting inflammation, hypolipidemia and/or neoplasia using amine-borane compounds.

2. Description of the Related Art

Various boron-containing compounds have previously been shown to exhibit therapeutic biological activity. For example, amineborane compounds such as amine.$BH_2COOH$, amine.$BH_2COOMe$ and amine.$BH_2CONHR$ have been demonstrated to exhibit antitumor, anti-inflammatory and hyperlipidemic activities. See, for example U.S. Pat. No. 4,312,989 issued to B. F. Spielvogel, et al, disclosing the use of amine-boranes to inhibit inflammation; see also Hall, Iris H., et al, *J. Pharm. Sci.*, 1981, 70, 339-341.

Several of the substituted borane adducts of amines have demonstrated significant anti-tumor activity in vivo (Hall, Iris H., et al, *J. Pharm. Sci.*, 1985, 74, 755-758; and Hall, Iris H., et al, *J. Pharm. Sci.*, 1979, 68, 685-688). These amine compounds are, with a few exceptions, derivatives of acyclic amines.

Spielvogel et al U.S. Pat. No. 4,312,989 discloses, inter alia, amine-boranes of the formula:

wherein:
X is selected from the group consisting of H, CN, and COOH; and
amine is selected from the group consisting of morpholine, N-methyl morpholine, pyridine, and cyanoethyldimethylamine.

Other literature articles relating to amine-borane compounds include: Mills, W. J. et al, "Synthesis and Characterization of Amine-Alkylcyanoboranes," *Inorg. Chem.*, 1990, 29, 302-308; Dalacker, F., et al "Amine-Carbamoyl-$^{10}$B-borane, Darstellung Und Biologische Eigenschaften," *Z. Naturforsch.*, 40 C., 344-350 (1985); Mills, W. J., et al, "Synthesis of Quinuclidine-Benzyl (ethylcarbamoyl)borane: The First Boron Analogue of a Phenylalanine Derivative," *J. Chem. Soc., Chem. Commun.*, 1989, 900-902; Spielvogel, B. F., et al, "Synthesis of Some Cyano-, Amido- and Carboxyborane Adducts of Amines and Diamines," *J. Inorg. Nucl. Chem.*, 41, 1223-1227 (1979); Mills, W. J., et al "Boron Analogues of Valine, Leucine, Isoleucine, and Phenylalanine: Syntheses of Amine-Alkyl (N-ethylcarbamoyl)-boranes," *Inorg. Chem.*, 1991, 30, 1046-1052; Weidig, C., et al, "Synthesis and Mechanism of Hydrolysis of Amine-Cyanoboranes," *Inorg. Chem.*, 13 (7), 1763-1768 (1974); Wisian-Neilson, P., et al, "A General Synthesis of Amine-Cyanoboranes, " *Inorg. Chem.*, 17(8) 2327-2329 (1978); Kemp, B., et al, "Synthesis and Characterization of the Cyano-and Carboxyborane Adducts of Quinuclidine," *Inorg. Chem.*, 23, 3063-3065 (1984); Das, M. K., et al, "Synthesis and Characterization of Pseudohaloborane Adducts of Some Heteroaromatic N-Bases," *Inorganic Chimica Acta,* 172, 35-39 (1990); Mittakanti, M., et al, "Synthesis and Characterization of Derivatives of Pyridine-Borane Adducts," *Inorg. Chem.*, 29, 554-556 (1990); and Martin, D. R., et al, "Reactions of Cyanotrihydroborate Ion and Its Derivatives With Halogens," *J. Inorg. Nucl. Chem.* 40, 9-13 (1978).

It is an object of the present invention to provide new amine-borane derivatives, including active anti-inflammatory, anti-hyperlipidemic, anti-neoplastic, and/or enzyme (e.g., DNA topoisomerase)- inhibiting agents.

Other objects and advantages will be more fully apparent from the ensuing disclosure and appended claims.

SUMMARY OF THE INVENTION

The heterocyclic amine-borane compounds of the present invention correspond to the general formula:

wherein:
A is a heterocyclic amine moiety selected from the group consisting of piperidine, substituted piperidine, piperazine, substituted piperazine, imidazole, substituted imidazole, pyrazole, substituted pyrazole, pyrazine, substituted pyrazine, pyrrole, substituted pyrrole, pyrrolidine, substituted pyrrolidine, indole, substituted indole, indoline, substituted indoline, quinoline, substituted quinoline, isoquinoline, substituted isoquinoline, thiazole, substituted thiazole, oxazole, substituted oxazole, thiazolidine, and substituted thiazolidine, wherein substitution is at any or all substituent positions, and comprises substituents selected from the group consisting of alkyl (preferably $C_1$-$C_{10}$ linear or branched alkyl), alkylaryl, aryl, aralkyl, nitro, alkoxy, hydroxy, cyano, thiol, and halo;

$R_1$ is selected from H, alkyl (preferably $C_1$-$C_{10}$ linear or branched alkyl), alkylaryl, aryl, and arylalkyl; and $R_2$ is selected from CN, COOH, $COOR_3$, and $CONHR_3$ where $R_3$ is selected from H, alkyl (preferably $C_1$-$C_{10}$ linear or branched alkyl), alkylaryl, aryl, and aralkyl.

In another aspect, the present invention relates to a method for inducing anti-hyperlipidemic activity in an animal, e.g., a mammalian subject, comprising administering to the animal subject a therapeutic (anti-hyperlipidemically effective) amount of a heterocyclic amine-borane compound of the above-described type.

A further aspect of the invention relates to a method for inducing antineoplastic activity in an animal, comprising administering to such animal a therapeutic amount of a heterocyclic amine-borane compound of the above-described type.

In a still further aspect, the present invention relates to a method of combatting inflammation in an animal, comprising administering to such animal a therapeutic (inflammation-combatting) amount of a heterocyclic amine-borane compound of the above-described type.

In yet another aspect, the present invention relates to a method of inhibiting enzyme (e.g., DNA topoisomerase, PRPP amidotransferase, IMP dehydrogenase, dihydrofolate reductase, ribonucleotide reductase, thymidine kinase, and/or TDP kinase activity in an animal subject, comprising administering to such animal subject enzyme-inhibitingly effective amount of a heterocyclic amine-borane adduct of the present invention. In a related aspect, the present invention relates to a method of inhibiting activity of enzymes of such type in vitro, comprising administering to an enzyme-containing material an enzyme-inhibitingly effective amount of a heterocyclic amine-borane adduct of the present invention.

In still another aspect, the present invention relates to a method of inhibiting DNA topoisomerase II activity in an in vivo or in vitro system, comprising administering to the system a DNA topoisomerase II enzyme-inhibitingly effective amount of a Lewis base-borane adduct.

The Lewis base-borane compounds usefully employed in the inhibition of DNA topoisomerase II enzyme activity may suitably comprise any of a wide variety of DNA topoisomerase II enzyme inhibitingly-effective Lewis base-borane adducts therefor, including: compounds disclosed in "Organoborane Chemistry," by T. Onak, Academic Press, New York, 1975; the amine-boranes described in the various technical literature articles and U.S. Pat. No. 4,312,989 referenced hereinabove in the "Background of the Invention" section hereof; phosphine-borane adducts; as well as the phosphite-borane compounds disclosed and claimed in U.S. Pat. No. 07/701,682 filed May 10, 1991 in the names of B. F. Spielvogel, et al. The disclosures of all of these references are hereby incorporated by reference herein.

As used herein, the term "Lewis base" means an electron donor moiety which is covalently, ionically, and/or associatively bonded to the boron atom of the borane moiety of the resulting adduct, or compound.

Other aspects and features of the present invention will become more fully apparent from the ensuing disclosure and appended claims.

DETAILED DESCRIPTION OF THE INVENTION, AND PREFERRED EMBODIMENTS THEREOF

The heterocyclic amine-borane compounds of the present invention correspond to the general formula:

$$A-\underset{\underset{R_1}{|}}{\overset{\overset{H}{|}}{B}}-R_2$$

wherein:

A is a heterocyclic amine moiety selected from the group consisting of piperidine, substituted piperidine, piperazine, substituted piperazine, imidazole, substituted imidazole, pyrazole, substituted pyrazole, pyrazine, substituted pyrazine, pyrrole, substituted pyrrole, pyrrolidine, substituted pyrrolidine, indole, substituted indole, indoline, substituted indoline, quinoline, substituted quinoline, isoquinoline, substituted isoquinoline, thiazole, substituted thiazole, oxazole, substituted oxazole, thiazolidine, and substituted thiazolidine, wherein substitution is at any or all substituent positions, and comprises substituents selected from the group consisting of alkyl (preferably $C_1$–$C_{10}$ linear or branched alkyl), alkylaryl, aryl, aralkyl, nitro, alkoxy, hydroxy, cyano, thiol, and halo;

$R_1$ is selected from H, alkyl (preferably $C_1$–$C_{10}$ linear or branched alkyl), alkylaryl, aryl, and arylalkyl; and $R_2$ is selected from CN, COOH, COOR$_3$, and CONHR$_3$ where R$_3$ is selected from H, alkyl (preferably $C_1$–$C_{10}$ linear or branched alkyl), alkylaryl, aryl, and aralkyl.

In the heterocyclic amine-borane derivatives of the foregoing formula, when any of the amine (A) substituents, or $R_1$, or $R_3$, is $C_1$–$C_{10}$ alkyl, the alkyl radical may be branched or linear in character. When these substituents, or any of them, is alkylaryl or aralkyl, the alkyl moiety of such radicals may likewise be either linear or branched in character.

It is to be appreciated that the aliphatic and/or aromatic substituents referred to above may optionally be substituted with heteroatoms or otherwise further substituted, subject to the proviso that such substitution does not preclude the utility of the resulting compound.

Illustrative heterocyclic amine-borane compounds of the present invention include the following:

| Compound No. | Structure |
| --- | --- |
| 1. | ⬡N(H)BH$_2$CN |
| 2. | HN⬡N(H)BH$_2$CN |
| 3. | ⬡N(H)BH$_2$COOH |
| 4. | HN⬡N(H)BH$_2$COOH |
| 5. | Ph—⬡N(H)BH$_2$COOH |
| 6. | Ph—⬡N(H)BH$_2$COOMe |
| 7. | Me—⬡N(H)BH$_2$COOH |
| 8. | Me—⬡N(H)BH$_2$COOMe |
| 9. | MeN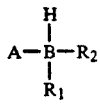NBH$_2$COOH |

| Compound No. | Structure |
| --- | --- |
| 10. | HN⌒NBH₂CN (pyrrole-like ring) |
| 11. | MeN⌒NBH₂CN |
| 12. | HN⌒NBH₂CN with Me substituent |
| 13. | MeN⌒NBH₂COOMe |
| 14. | MeN⌒NBH₂C(O)NHEt |
| 15. | 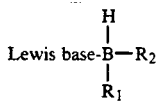 HN⌒NBH₂CN with Me |
| 16. | HN⌒NBH₂CN with Me |

In a specific aspect of the present invention, enzyme inhibitingly-effective Lewis base-borane adducts are employed as inhibitors of DNA topoisomerase II enzyme. The enzyme-inhibiting compounds of such type correspond to the general formula:

$$\text{Lewis base-}\overset{\overset{\displaystyle H}{|}}{\underset{\underset{\displaystyle R_1}{|}}{B}}-R_2$$

wherein:
the Lewis base moiety may be of any suitable type, as for example including amines, both heterocyclic as well as acyclic species, phosphine (—PR₂ R₂), or phosphite (R•O)₃P—, wherein each R• is independently selected from: H, $C_1$–$C_{10}$ alkyl; alkylaryl; aralkyl; aryl; nucleosides; monovalent metal ions; and quaternary ammonium cations of the formula $(R_a)_4N^+$, wherein each $R_a$ is independently selected from H and $C_1$–$C_{10}$ alkyl;

$R_1$ is H, alkyl (preferably $C_1$–$C_{10}$ linear or branched alkyl), alkylaryl, aralkyl, and aryl; and $R_2$ is selected from H, CN, COOH, COOR₃ or CONHR₃ where R₃ is H, alkyl, alkylaryl, aralkyl, and aryl, wherein the alkyl radical or moiety preferably is $C_1$–$C_{10}$ linear or branched alkyl.

In general, any suitable enzyme inhibitingly-effective Lewis acid-borane adducts may be employed in inhibition of the DNA topoisomerase II enzyme. Other enzyme inhibitingly-effective Lewis base-borane adducts potentially suitable for such purpose include the boron-containing compounds which are described in: "Organoborane Chemistry," T. Onak, Academic Press, New York, 1975; Spielvogel et al U.S. Pat. No. 4,312,989 and U.S. Pat. No. 4,368,194; Spielvogel et al U.S. Pat. Nos. 5,023,513 and 5,143,907, the disclosures of which hereby are incorporated herein by reference. Preferably, the enzyme-inhibitingly effective compounds comprise amine carboxyboranes, and corresponding esters and amides, wherein the amine moiety may be either cyclic (heterocyclic) or acyclic in character.

Inhibition of the topoisomerase II enzyme has been empirically linked to the anti-tumor properties of a number of agents such as actinomycin, anthracenediones, epipodophyllotoxin, isoflavonoids, benzisoquinolinediones, acridines, and alpha-boswellic acid (P. D'arpa and L. F. Liu, *Biochim. Biophy. Acta*, 1989, 163, 1989). Lewis acid-borane compounds have been demonstrated to be highly effective inhibitors of the topoisomerase II enzyme.

In addition to the inhibition of the topoisomerase II enzyme, the heterocyclic amine-borane compounds of the present invention also exhibit enzyme inhibiting activity for various other enzymes, including PRPP amidotransferase, IMP dehydrogenase, dihydrofolate reductase, and ribonucleotide reductase.

Exemplary of heterocyclic amine boranes of the present invention, and inclusive of borane species which may be usefully employed (e.g., in administration to an animal subject) to inhibit enzymes of the above-described type (e.g., DNA topoisomerase II enzyme), and/or to achieve therapeutic effects in combatting disease states (e.g., inflammation, hyperlipidemia, neoplasia, or combinations thereof), are the following illustrative compounds:

a. 1-Benzylimidazole-3-cyanoborane
b. 1-Methylimidazole-3-carboxyborane
c. 1-Methylimidazole-3-carbomethoxyborane
d. 1-Methylimidazole-3-(N-ethylcarbamoyl)borane
e. 1-Methylimidazole-3-carboethoxyborane
f. 1,2-Dimethylimidazole-3-carboxyborane
g. Imidazole-3-carboxyborane
h. 2-Methylimidazole-3-cyanoborane
i. 4-Methylimidazole-3-carboxyborane
j. 5-Methylimidazole-3-cyanoborane
k. 2-Ethylimidazole-3-carboxyborane
l. 2-Ethyl-4-methylimidazole-3-cyanoborane
m. 4-hydroxymethylimidazole-3-cyanoborane
n. 2-Mercaptoimidazole-3-cyanoborane
o. 2-Methyl-5-nitroimidazole-3-cyanoborane
p. 2-Nitroimidazole-3-cyanoborane
q. 4-Phenylimidazole-3-cyanoborane
r. 4-Nitroimidazole-3-cyanoborane
s. Piperazine-1-carboxyborane
t. Piperazine-1-cyanoborane
u. 1-(2-Methoxyphenyl)piperazine-4-cyanoborane
v. 1-Methylpiperazine-1-carboxyborane
w. 2-methylpiperazine-1-carboethoxyborane
x. Piperidine-1-(N-ethylcarbamoyl)borane
y. 2-Methylpiperidine-1-carboethoxyborane
z. 4-Methylpiperidine-1-carbomethoxyborane
aa. 4-Phenylpiperidine-1-carboxyborane
ab. 4-Aminomethylpiperidine-1-cyanoborane
ac. 4-Benzylpiperidine-1-carboxyborane
ad. 1(2-chlorethyl)piperidine-1-cyanoborane
ae. 2,6-Dimethylpiperidine-1-cyanoborane
af. 4-Hydroxypiperidine-carbomethoxyborane
ag. Pyrazine-1-carboxyborane ah. Pyrazine-1-cyanoborane
ai. Pyrazole-2-cyanoborane
aj. Pyrrole-1-carboxyborane
ak. Pyrrolidine-1-carbomethoxyborane
al. Indole-1-cyanoborane
am. Indoline-1-cyanoborane
an. Quinoline-1-cyanoborane
ao. 8-Methylquinoline-1-carboxyborane
ap. Isoquinoline-2-cyanoborane
aq. 3-Isoquinolinecarbonitrile-2-cyanoborane
ar. Thiazole-3-carboxyborane
as. Thiazolidine-4-carboxylic acid-3-cyanoborane
at. Oxazole-3-cyanoborane In general, the amine-borane, phosphine-borane, and phosphiteborane compounds usefully employed in effecting DNA topoisomerase II enzyme inhibition in accordance with the present invention, may usefully be synthesized by known methods, such as those set out in the references identified hereinabove and the novel heterocyclic amine compounds of the present invention usefully employed in effecting enzyme inhibition and/or combatting various disease states (e.g., inflammation, hyperlipidemia, and/or neoplasia) may be synthesized by synthetic methods correspondent or analogous to those employed in synthesis of amine-boranes of previously known character, e.g., the amine-boranes disclosed in U.S. Pat. No. 4,312,989.

By way of example, amine-cyanoboranes may be prepared by either of (1) amine exchange with anilinecyanoborane or (2) by reaction of amine hydrochlorides with sodium cyanoborohydride. Amine exchange is efficient when the specific amine employed has high basicity and/or is not excessively bulky. Reaction with nonaromatic secondary cyclic amines yields exclusively the exchange product. The exchange reaction can be performed either in excess amine or by using equimolar amounts of reactants in a solvent.

Cyanoborane derivatives of imidazoles may be advantageously prepared by reaction of amine hydrochlorides with sodium cyanoborohydride. The reaction of sodium cyanoborohydride with various imidazole hydrochlorides yielded corresponding imidazole-$N^3$-cyanoboranes. In the case of 4-methylimidazole hydrochloride, both 4-methylimidazole-$N^3$-cyanoborane and 5-methylimidazole-$N^3$-cyanoborane were obtained in approximately 1:1 ratio. The formation of these two isomers may be explained by the fact that except for N-methylimidazole hydrochloride, the reaction can occur at either nitrogen for all other hydrochlorides. For imidazole or 2-methyl imidazole, the same product is obtained by reaction at either site. In the case of the 4-methylderivative, however, reaction at different nitrogen sites gives different isomers Apparently, the presence of the methyl group does not adversely affect the amount of coordination on the adjacent nitrogen atom.

Conversion to carboxyborane derivatives can be achieved by (1) amine exchange or (2) alkylation of cyanoborane followed by hydrolysis. The alkylation/hydrolysis method, however, cannot be used with primary or secondary amine-cyanoboranes, since it leads to decomposition.

Carboxyboranes may be prepared by amine exchange with trimethylamine-carboxyborane. Even when nonaromatic amines having equivalent or lower basicity than trimethylamine are employed, the reaction proceeds if the amine is suitably small in steric bulk. Other Lewis base-carboxyborane species such as triphenylphosphinecarboxyborane can also be used as substrates for Lewis base exchange. The reaction may be performed in excess amine, when the amine employed is liquid at room temperature, and may be conducted in a suitable solvent, e.g., tetrahydrofuran, when the amine is a solid.

Amine-carbomethoxyboranes and N-methylimidazole-N-ethylcarbamoylborane may also be prepared by exchange with corresponding trimethylamine or other Lewis base derivatives. 4-Methyl-piperidine and N-methylimidiazole derivatives may be prepared using excess amine as solvent, and 4-phenylpiperidine-carbomethoxyborane may be prepared in refluxing tetrahydrofuran.

The compounds of the present invention have pharmaceutical activity, including enzyme-inhibiting, anti-inflammatory, anti-hyperlipidemic, and anti-neoplastic activity, and are useful in treating animals, e.g., mammals, for deleterious enzyme-mediated conditions, inflammation, hyperlipidemia, and neoplasia conditions.

A method of inhibiting enzyme activity of DNA topoisomerase II enzyme, in an animal subject in need of such treatment, comprises administering to the animal subject an enzyme-inhibitingly effective amount of a Lewis base-borane compound.

A method of inhibiting enzyme activity of enzymes such as PRPP amidotransferase, IMP dehydrogenase, dihydrofolate reductase, and/or ribonucleotide reductase, in an animal subject in need of such treatment, comprises administering to the animal subject an enzyme-inhibitingly effective amount of a heterocyclic amine-borane compound of the present invention.

A method of combatting hyperlipidemia in an animal subject in need of such treatment comprises administering to the animal subject a hyperlipidemia-combatting amount of a heterocyclic amine-borane compound of the present invention.

A method of producing an anti-inflammatory responce in an animal subject in need of such treatment comprises administering to the animal subject an inflammation-combatting amount of a heterocyclic amine-borane compound of the present invention.

A method of combatting tumors in an animal subject in need of such treatment comprises administering to the animal subject a tumor-combatting amount of a heterocyclic amine-borane compound of the present invention.

A method of combatting tumors, preferably solid tumors (e.g., adenocarcinoma, bronchogenic carcinoma, osteosarcoma, epidermoid carcinoma, breast carcinoma, glioma) in an animal subject in need to such treatment comprises administering to the animal subject a tumor-combatting amount of a heterocyclic amine-borane compound of the present invention, after which the tumor preferably is exposed to thermal radiation (low energy neutrons) in an amount effective for $^{10}B$ located in the tumor (by virtue of the administration of the heterocyclic amine compound to the subject) to capture a neutron, decay, and release an alpha particle in cells of the tumor.

The neoplastic conditions against which heterocyclic amine-borane compounds of the present invention may advantageously be employed include lymphoid leukemia, lymphoblastic leukemia, and cervical carcinoma, as well as colorectal adenocarcinoma, KB nasopharynx and osteosarcoma, and lung bronchogenic and glioma growth.

Boron derivatives of piperidine, piperazine, and imidazole are preferred classes of boron derivatives which may be advantageously employed in combatting tumors, and are also preferred in the broad practice of the present invention in other pharmaceutical applications.

Subjects to be treated by the method of the present invention include both human and non-human animal (e.g., bird, dog, cat, cow, horse) subjects, and are preferably mammalian subjects.

The heterocyclic amine-borane compounds of the present invention have also been discovered to be potent inhibitors of the DNA topoisomerase II enzyme. Inhibition of this enzyme has been linked to the antitumor properties of a number of pharmaceutical agents such as actinomycin, anthracenediones, epipodophyllotoxin, isoflavonoids, benzisoquinolinediones, acridines, and alpha-boswellic acid.

In addition to the heterocyclic amine-borane compounds of the present invention, it has been discovered that borane compounds, preferably base-borane compounds and especially amine carboxyboranes, and corresponding esters and amides have an inhibitory affect on DNA topoisomerase II enzyme activity, and that heterocyclic amine-borane compounds of the present invention have an inhibitory affect on the activity of various other enzymes, e.g., PRPP amidotransferase, IMP dehydrogenase, dihydrofolate reductase, and/or ribonucleotide reductase. Accordingly, the present invention comprehends a method of inhibiting such enzyme(s), by administration to an animal subject of an enzyme (e.g., DNA topoisomerase II) inhibitingly effective amount of the boron-based compound. Such borane compounds may also be potentially usefully employed in in vito inhibition of enzymes in extracorporeal material containing same.

In the broad method aspects of the present invention, as directed to combatting various physiological conditions and/or inhibiting enzyme activity, as described hereinabove, animal subjects typically may be administered boron-containing compounds of appropriate utility in any suitable dose which is appropriate to the physiological condition, and not contraindicated by other operative corporeal factors. Typically, a daily dose of at least about 0.1 mg/kg weight of the animal subject, more preferably at least about 0.5 mg/kg, and most preferably at least about 2 mg/kg, on the same basis, may be usefully employed. The daily dose preferably is not more than about 1,000 mg/kg, more preferably not more than about 200 mg/kg, and most preferably not more than about 50 mg/kg, on the same animal weight basis.

In such treatment methods, the boron-based compounds may be administered per se or in the form of pharmaceutically acceptable salts. When used in medicine, the salts of such compounds should be both pharmacologically and pharmaceutically acceptable, but nonpharmaceutically acceptable salts may conveniently be used to prepare the free active compounds or pharmaceutically acceptable salt thereof and are not excluded from the scope of the general invention. Where appropriate, such pharmacologically and pharmaceutically acceptable salts include, but are not limited to, those prepared from the following bases: sodium hydroxide, potassium hydroxide, ammonium hydroxide, and calcium hydroxide.

The present invention also comprehends pharmaceutical formulations, both for veterinary and for human medical use, which comprise the active agent (the boron-based compound) together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in the quantity appropriate to achieve the desired daily dose.

The formulations include those suitable for oral, rectal, topical, nasal, ophthalmic, or parenteral (including subcutaneous, intramuscular and intravenous) administration. Formulations suitable for parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compounds into association with a liquid carrier, a finely divided solid carrier, or both, and then, if necessary, shaping the product into desired formulations.

Formulations of the present invention suitable for oral administration may be presented as discrete units such as capsules, cachets, tablets, or lozenges, each containing a predetermined amount of the active ingredient as a powder or granules; or a suspension in an aqueous liquor or non-aqueous liquid such as a syrup, an elixir, an emulsion, or a draught.

A tablet may be made by compressure or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservatives, agents to retard crystallization of the sugar, and agents to increase the solubility of any other ingredient, such as a polyhydroxy alcohol, for example glycerol or sorbitol.

Formulations suitable for parenteral administrations suitably comprise a sterile aqueous preparation of the active compound, which preferably is isotonic with the blood of the recipient (e.g., physiological saline solution).

Nasal spray formulations comprise purified aqueous solutions of the active compounds with preservative agents and isotonic agents. Such formulations preferably are adjusted to a pH and isotonic state compatible with the nasal mucose membranes.

Formulations for rectal administration may be presented as a suppository with a suitable carrier such as cocoa butter, hydrogenated fats, or hydrogenated fatty carboxylic acids.

Ophthalmic formulations may be prepared by a similar method to the nasal spray, except that the pH and isotonic factors are preferably adjusted to match those of the eye.

Topical formulations comprise the active compound dissolved or suspended in one or more media, such as mineral oil, petroleum, polyhydroxy alcohols, or other bases used for topical pharmaceutical formulations.

In addition to the aforementioned ingredients, the formulations of the present invention may further include one or more accessory ingredient(s) selected from diluents, buffers, flavoring agents, binders, disintegrants, surface active agents, thickeners, lubricants, preservatives (including antioxidants), and the like.

The following examples are provided to illustrate the present invention, and should not be construed as limiting thereof. In the examples, compounds may be identified in the first instance by a name and a reference number, and thereafter may be identified solely by reference number, for ease of reference.

In the ensuing examples, IR spectra were recorded on a Perkin-Elmer 297 spectrometer. Spectra were obtained as thin films of nujolmulls using sodium chloride plates and calibrated using a standard polystyrene film. $^1H$ NMR spectra were recorded on a Varian XL300 spectrometer. $^{11}B$ and $^{13}C$ NMR spectra were recorded on a JEOL FX 90Q spectrometer. Chemical shifts were with respect to $Me_4Si$ for $^1H$ and $^{13}C$ NMR spectra and $BF_3Et_2O$ for $^{11}B$ NMR spectra with more positive values of the chemical shift representing deshielding. Elemental analyses were performed by Galbraith Labs, Inc. (Tennessee).

EXAMPLE I

Preparation of Amine-Cyanoborane by Exchange in Excess Amine

Aniline-cyanoborane (4.14 g. 31.4 mmol) was taken in piperidine (40 ml) and was heated at 60°-65° C. for 7 hr. The excess piperidine was removed by vacuum distillation. The final traces of amine were removed by pumping overnight under the vacuum. The residue was crystallized twice from diethylether/pentane.

EXAMPLE II

Preparation of Amine-Cyanoborane by Exchange Using Equimolar Amounts of Aniline Cyanoborane and Amine Equimolar amounts of aniline-cyanoborane and an amine were taken in anhydrous THF (50 ml) under an inert atmosphere. The mixture was heated at reflux for 24 hour. The solvent was removed under reduced pressure. With piperazine as the amine, the residue was washed with diethylether and crystallized from dichloromethane/pentane.

EXAMPLE III

Preparation of Amine-Cyanoborane by Reaction of Sodium-Cyanoborohydride With an Amine-Hydrochloride To a solution of hydrogen chloride in an appropriate solvent at 0° C. was slowly added a solution of ca. 1 equivalent of an amine in that solvent. The solvent used for N-methylimidazole was diethylether; the solvent for 2-methylimidazole was dichloromethane; and the solvent for 4-methylimidazole was methanol. After complete addition, the mixture was allowed to warm to room temperature and stirred for several hours. N-Methylimidazole hydrochloride was insoluble in the solvent used. It was filtered under $N_2$ and dried in vacuo. In the other cases, the solvent was removed under reduced pressure to give a solid. These hydrochlorides were used without any purification.

To a solution of sodium cyanoborohydride (0.09 mol) in anhydrous THF (140 ml) under $N_2$ was added an amine-hydrochloride (ca. 50% excess). The mixture was heated at reflux and the progress of reaction was followed by $^{11}B$ NMR. After ca.>95% reaction, the mixture was cooled to room temperature, filtered and solvent was removed under reduced pressure. The residue was dissolved in ethyl acetate (150 ml) and was washed with water (3×50 ml). The organic layer was dried over anhydrous sodium sulfate, filtered and solvent was removed under reduced pressure to give the product. 2-Methylimidazole-$N^3$-cyanoborane was further purified by crystallization from THF/pet. ether. The product from the reaction of 4-methylimidazole-hydrochloride was passed through a silica gel column using diethylether:dichloromethane (6:4) to give a white solid which showed two sets of peaks in $^1H$ and $^1C$ NMR spectra.

EXAMPLE IV

Preparation of Amine Carboxyboranes by Exchange in Excess Amine

Trimethylamine-carboxyborane (27 mmol) was taken in an excess of desired amine (25 ml) and heated at 65°-70° C. for several hours. The excess amine was removed by vacuum distillation. The final traces of amine were removed by vacuum pumping overnight and the residue was purified as follows: piperidine carboxyborane-crystallized from dichloromethane/pentane; morpholine-4-carboxyborane-crystallized twice from dichloromethane/pentane; 4-methylpiperidine carboxyborane-crystallized from diethylether; N-methylimidazole-$N^3$-carboxyborane-washed with dichloromethane.

EXAMPLE V

Preparation of Amine-Carboxyboranes by Exchange Using Equimolar Amounts of Trimethylamine-Carboxyborane and an Appropriate Amine Equimolar amounts of trimethylamine-carboxyborane and an appropriate amine were taken in anhydrous THF under $N_2$. The mixture was heated at reflux and the reaction was followed by $^{11}B$ NMR. In the case of piperazine as the amine, the product was filtered and washed with THF. For 4-phenylpiperidinecarboxyborane, the solvent was removed under reduced pressure and the residue was crystallized from dichloromethane.

EXAMPLE VI

Preparation of Amine-Carboxyboranes Via Intermediate Generation of Nitrilium Salt Amine-cyanoborane (8.25 mmol) and a solution of triethyloxonium tetrafluoroborate (2 equivalent of 1M solution in anhydrous dichloromethane) were heated at reflux for 24 hour. The solvent was removed under reduced pressure and the residue was kept in vacuo overnight. It was taken in water (6.5 ml) and was stirred at room temperature. The reaction was followed by $^{11}B$ NMR.

EXAMPLE VII

Preparation of Amine-Carbomethoxyboranes by Exchange in Excess Amine

Trimethylamine-carbomethoxyborane (15.27 mmol) was taken in an excess of desired amine (25 ml) under N$_2$ and was heated at 65°-70° C. for 16 hour. The excess amine was removed by vacuum distillation followed by pumping overnight on a vacuum line. The residue was purified as follows: 4-methyl-piperidine-carbomethoxyborane-crystallized from diethyl ether; N-Methylimidazole-N$^3$-carbomethoxyborane (stirred with diethyl ether, filtered and washed with ether).

EXAMPLE VIII

Preparation of Amine-Carbomethoxyboranes by Exchange Using Equimolar Amounts of Trimethylamine-Carbomethoxyborane and an Appropriate Amine Equimolar amounts of trimethylamine-carbomethoxyborane (7.63 mmol) and an amine were taken in a dry solvent under N$_2$ and were heated at reflux. The reaction was followed by $^{11}$B NMR. For 4-phenyl-piperidine, the solvent (THF) was removed under reduced pressure. n-Pentane was added to the residue, stirred to yield a fine powdery suspension and then filtered and washed twice with n-pentane.

EXAMPLE IX

Preparation of Amine-N-Ethylcarbamoyl borane by Exchange Reaction

Tirmethylamine-N-ethylcarbamoyl borane (7.43 mmol) was taken in excess N-methylimidazole (20 ml) and the mixture was heated at 60° C. for 17½ hour. The excess imidazole was removed by vacuum distillation followed by pumping overnight on a vacuum line. The yellow residue was taken in diethylether, stirred and filtered to give a sticky solid. It was dissolved in chloroform and treated with activated charcoal to remove the colored impurities. Attempted crystallization was unsuccessful. It was purified by flash chromatography on silica gel dichloromethane: methanol (9.5:0.5).

Set out below in Table I is an identification, by compound number, as well a chemical structure, of compounds synthesized in accordance with above-described synthesis techniques.

TABLE I

| Compound No. | Structure |
|---|---|
| 1 | 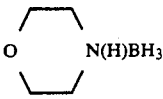 |
| 2 | 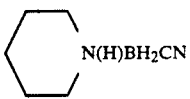 |
| 3 | 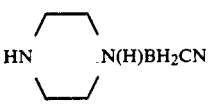 |
| 4 | 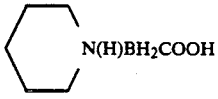 |
| 5 | 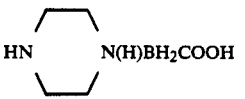 |
| 6 | 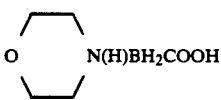 |
| 7 | 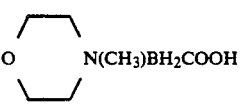 |
| 8 | 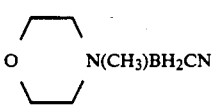 |
| 9 | 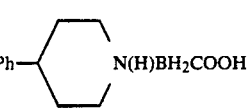 |
| 10 | 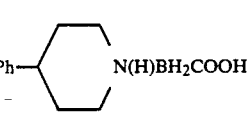 |
| 11 | 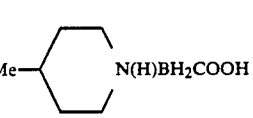 |
| 12 | 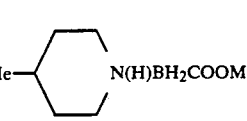 |
| 13 | 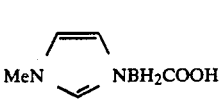 |
| 14 | 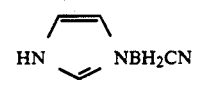 |
| 15 | 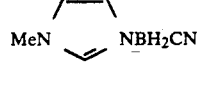 |
| 16 | 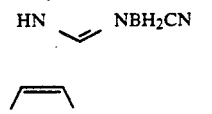 |
| 17 | 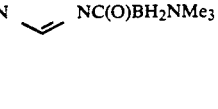 |

TABLE I-continued

| Compound No. | Structure |
|---|---|
| 18 | MeN⟨=⟩NBH₂COOMe (imidazole ring) |
| 19 | MeN⟨=⟩NBH₂C(O)NHEt (imidazole ring) |
| 20 | HN⟨=⟩NBH₂CN with Me substituent (methylimidazole) |
| 21. | HN⟨=⟩NBH₂CN with Me substituent (methylimidazole) |

Note: Compounds 1, 6–8, and 17 are previously known compounds (e.g., see Spielvogel et al U.S. Pat. No. 4,312,989), but are included here for comparison purposes.

In connection with the foregoing examples, various reagents and compounds were prepared by previously described techniques, as follows: aniline-cyanoborane (Wisian-Nielson, P., et al, *Inorg. Chem.*, 1978, 17, 2327); trimethylamine-carboxyborane (Spielvogel, B. F., et al, *J. Am. Chem. Soc.*, 1976, 98, 5702); trimethylamine-carbomethoxyborane (Spielvogel, B. F., et al, *J. Inorg. Chem.*, 1984, 23, 4322); trimethylamine-N-ethyl-carbamoylborane (Spielvogel, B. F., et al, *Inorg. Chem.*, 1984, 23, 1776); N-methylmorpholine-4-cyanoborane (Spielvogel, B. F., et al, *J. Inorg. Nucl. Chem.*, 1979, 41, 1223); and trimethylamine-imidazole carbonyldihydroborane (Dollcker, F., et al, *Z. Naturforsch*, 1985, 40C, 344–349). Morpholine-4-borane, morpholine, N-methylmorpholine, piperidine, piperazine, 4-methylpiperidine, 4-phenylpiperidine, imidazole, imidazole hydrochloride, N-methylimidazole, 2-methylimidazole and 4-methylimidazole were obtained commercially and used as received. Tetrahydrofuran (THF) was dried by heating at reflux over sodium/benzophenone and distilled onto 4A molecular sieve. Dichloromethane was heated at reflux over phosphorous pentoxide and was stored over 4A molecular sieve. Anhydrous monoglyme was obtained from Aldrich Chemical Company and was used as received. All radioisotopes were purchased from New England Nuclear Company. All other chemicals were obtained from Sigma Chemical Company. GF/F and GF/B filters and PEI plates were purchased from Fisher Scientific Company.

All the products were characterized by $^1$H, $^{11}$B and $^{13}$C NMR. IR spectroscopies and elemental analyses. The spectroscopic data are presented in Tables 2 and 3. For all non-aromatic cyclic amine derivatives, second order proton NMR spectra were obtained. No attempts were made to calculate the coupling constants or to assign the peaks to axial or equatorial protons.

TABLE 2

| Compound # | Method of Prep. | % Yield | MP/ °C. | IR(nujol) (BH) (CN) | (CO) | $^{11}$B NMR/ ppm (Solvent) | $^1J_{BH}$/Hz | % C | % H | % N | % B |
|---|---|---|---|---|---|---|---|---|---|---|---|
| | | | | | | | | \multicolumn{4}{c}{Elemental Analyses; Calc (found)} |
| 2 | 1a | 61.5 | 76–77 | 2420 & 2405 cm$^{-1}$ | 2205 cm$^{-1}$ | −19.3 (CDCl₃) | 95 ± 1 | 58.12 (58.46) | 10.57 (10.82) | 22.59(22.84) | 8.72 (9.06) |
| 3 | 1b | 59.4 | 140–141 | 2405 cm$^{-1}$ | 2205 cm$^{-1}$ | −19.5 (DMSO-d₆) | a | 48.05 (47.58) | 9.68 (9.86) | 33.62(32.89) | 8.65 (9.04) |
| 4 | 3a | 57.1 | 121–122 | 2425, 2370 & 2295 cm$^{-1}$ | 1642 & 1637 cm$^{-1}$ | −13.8 (D₂O) | 94 ± 5 | 50.40 (50.42) | 9.87 (9.71) | 9.80(9.76) | 7.56 (7.94) |
| 5 | 3b | 92.7 | decomp above 153 | 2390 cm$^{-1}$ | 1650 cm$^{-1}$ | −13.6 (D₂O) | a | 41.71 (41.90) | 9.10 (9.20) | 19.46(19.40) | 7.51 (7.53) |
| 6 | 3a | 64.7 | 116–117.5 | 2420 & 2395 cm$^{-1}$ | 1642 cm$^{-1}$ | −13.8 (D₂O) | a | 41.43 (41.30) | 8.34 (8.61) | 9.66(9.64) | 7.46 (7.70) |
| 9 | 3b | 28.6 | 124.5–126.5 | 2390 cm$^{-1}$ | 1660 cm$^{-1}$ | −13.4 ((CD₃)₂CO) | a | 65.79 (65.23) | 8.28 (8.56) | 6.39(6.17) | 4.93 (4.97) |
| 10 | 5b | 85.4 | 100–102 | 2395 cm$^{-1}$ | 1655 cm$^{-1}$ | −13.8 (CDCl₃) | a | 66.98 (66.60) | 8.65 (8.87) | 6.01(6.05) | 4.64 (4.44) |
| 11 | 3a | 35.1 | 116–117 | 2395, & 2375 (sh) 2300 cm$^{-1}$ | 1665 cm$^{-1}$ | −13.8 (CDCl₃) | a | 53.55 (53.75) | 10.27 (10.31) | 8.92(8.98) | 6.88 (7.15) |
| 12 | 5a | 40.7 | 115–118 | 2395 & 2305 cm$^{-1}$ | 1645 cm$^{-1}$ | −13.6 (CDCl₃) | 93 ± 2 | 56.18 (56.29) | 10.61 (10.26) | 8.19(8.12) | 6.32 (6.12) |
| 13 | 3a | 85.7 | 138–140 | 2395 & 2290 cm$^{-1}$ | 1640 cm$^{-1}$ | −16.9 (DMSO-d⁶) | a | 42.91 (42.78) | 6.48 (6.77) | 20.02(20.24) | 7.72 (7.78) |
| 14 | 2 | 77.1 | 75–78.5 | 2430 & 2405 cm$^{-1}$ | 2205 cm$^{-1}$ | −22.5 ((CD₃)₂CO) | 102.5 | 44.93 (44.78) | 5.66 (5.78) | 39.30(39.55) | 10.11 (9.96) |
| 15 | 2 | 69.9 | 58.5–60.5 | 2410 cm$^{-1}$ | 2195 cm$^{-1}$ | −22.5 ((CD₃)₂CO) | 103 | 49.65 (49.14) | 6.67 (6.75) | 34.74(34.31) | 8.94 (8.68) |
| 16 | 2 | 57.1 | 116–118 | 2400 cm$^{-1}$ | 2205 cm$^{-1}$ | −23.5 ((CD₃)₂CO) | 101 ± 1 | 49.65 (49.56) | 6.67 (6.74) | 34.74(35.41) | 8.94 (9.01) |
| 18 | 5a | 87.2 | 56.5–58 | 2370 2285 cm$^{-1}$ | 1665 cm$^{-1}$ | −17.0 (CDCl₃) | 92 ± 2 | 46.80 (46.61) | 7.20 (7.23) | 18.19(18.58) | 7.02 (7.25) |
| 19 | 6 | 29.2 | 82–83 | 2300 cm$^{-1}$ | 1590 cm$^{-1}$ | −15.6 (CDCl₃) | 102 ± 1 | 50.34 (50.20) | 8.45 (8.42) | 25.16(24.90) | 6.47 (6.47) |
| 20 | 2 | 42.9 | 40–81 | 2415 & 2310 cm$^{-1}$ | 2210 & 2200 cm$^{-1}$ | −23.8 (CDCl₃) | a | — | — | — | — |

TABLE 3

$^{13}C$ and $^1H$ NMR Data

| Compound # | Solvent | $^{13}C$ NMR DATA[a] | Solvent | $^1H$ NMR DATA[b,c] |
|---|---|---|---|---|
| 2 | $CDCl_3$ | = 22.3 ppm, $C_4$; 24.3 ppm, $C_3$ & $C_5$; 51.9 ppm, $C_2$ & $C_6$ | $CDCl_3$ | = 1.38 ppm, $H_4$; 1.67 ppm & 1.80 ppm, $H_3$ & $H_5$; 2.54 ppm & 3.31 ppm, $H_2$ & $H_6$; 4.98 ppm, br., NH |
| 3 | DMSO-$d^6$ | = 43.8 ppm, $C_3$ & $C_5$; 51.0 ppm, $C_2$ & $C_6$ | DMSO-$d^6$ | = 1.53 ppm, br., $BH_2$; 2.44 ppm & 2.67 ppm, $H_3$ & $H_5$; 2.87 ppm, $H_2$ & $H_6$; 6.69 ppm, br., NH |
| 4 | DMSO-$d^6$ | = 22.6 ppm, $C_4$; 23.8 ppm, $C_3$ and $C_5$; 51.0 ppm, $C_2$ and $C_6$ | $D_2O$ | = 1.24 ppm, $H_4$; 1.42 ppm & 1.59 ppm, $H_3$ & $H_5$; 2.34 ppm & 3.02 ppm, $H_1$ & $H_6$ |
| 5 | DMSO-$d^6$ | = 43.8 ppm, $C_3$ & $C_5$; 51.0 ppm, $C_2$ & $C_6$ | $D_2O$ | = 1.58 ppm, br., $BH_2$; 2.64 ppm and 2.92 ppm, $H_3$ and $H_5$; 3.10 ppm, $H_2$ and $H_6$ |
| 6 | DMSO-$d^6$ | = 50.1 ppm, $C_3$ & $C_5$; 64.5 ppm, $C_2$ & $C_6$ | $D_2O$ | = 1.64 ppm, br., $BH_2$; 2.67 ppm & 3.00 ppm, $H_3$ & $H_5$; 3.58 ppm and 3.82 ppm, $H_2$ and $H_6$ |
| 9 | $(CD_3)_2CO$ | = 32.7 ppm, $C_3$ & $C_5$; 41.3 ppm, $C_4$; 52.5 ppm, $C_2$ & $C_6$; 127.1 ppm, $C'_4$; 127.5 ppm, $C'_3$ & $C'_5$; 129.3 ppm, $C'_2$ & $C'_6$; 146.2 ppm, $C'_1$ | $(CD_3)_2CO$ | = 1.54–1.82 ppm, $H_3$ & $H_5$; 2.40 ppm, $H_2$ & $H_6$; 2.52 ppm, $H_4$; 4.88 ppm, br., NH; 6.83–7.05 ppm, aromatic; 9.43 ppm, br., OH |
| 10 | $CDCl_3$ | = 32.5 ppm, $C_3$ & $C_5$; 40.6 ppm, $C_4$; 48.7 ppm, $OCH_3$; 52.2 ppm, $C_2$ & $C_6$; 126.4 ppm, $C'_3$ & $C'_5$; 126.8 ppm, $C'_4$; 128.7 ppm $C'_2$ and $C'_6$; 144.1 ppm, $C'_1$ | $CDCl_3$ | = 1.92 ppm & 1.95 ppm, $H_3$ & $H_5$; 2.73 ppm, $H_4$; 2.73 ppm & 3.45 ppm, $H_2$ & $H_6$; 3.56 ppm, s, $OCH_3$; 4.77 ppm, br., NH, 7.19–7.35 ppm, aromatic H |
| 11 | $CDCl_3$ | = 21.6 ppm, $CH_3$; 29.4 ppm, $C_4$; 33.6 ppm, $C_3$ & $C_5$; 52.0 ppm, $C_2$ & $C_6$ | $CDCl_3$ | = 0.97 ppm, d, $^3J_{H,H}$ = 6.6Hz, $CH_3$; 1.29 ppm & 1.78 ppm, $H_3$ & $H_5$; 1.56 ppm, $H_4$; 2.55 ppm & 3.30 ppm, $H_2$ & $H_6$; 4.50 ppm, br., NH; 9.15 ppm, br., OH |
| 12 | $CDCl_3$ | = 21.6 ppm, $CH_3$; 29.4 ppm, $C_4$; 33.5 ppm, $C_3$ & $C_5$; 48.5 ppm, $OCH_3$; 52.0 ppm, $C_2$ & $C_6$ | $CDCl_3$ | = 0.97 ppm, d, $^3J_{H,H}$ = 7Hz, $CH_3$; 1.33 ppm & 1.80 ppm, $H_3$ and $H_5$; 1.57 ppm, br., $H_4$; 2.57 ppm & 3.31 ppm, $H_2$ & $H_6$; 3.58 ppm, s, $OCH_3$; 4.24 ppm, br., NH |
| 13 | DMSO-$d^6$ | = 34.4 ppm, $CH_3$; 121.8 ppm, $C_4$; 126.2 ppm, $C_5$; 138.1 ppm; $C_2$ | DMSO-$d^6$ | = 2.38 ppm, br., $BH_2$; 3.61 ppm, s, $NCH_3$; 6.95 ppm, s, $H_5$; 7.22 ppm, s, $H_4$; 8.23 ppm, s, $H_2$; 9.86 ppm, s, OH |
| 14 | $CDCl_3$ | = 118.3 ppm, $C_4$; 125.6 ppm, $C_5$; 135.4 ppm; $C_2$ | $(CD_3)_2CO$ | = 2.50 ppm, br., $BH_2$; 7.16 ppm, s, $H_5$; 7.25 ppm, s, $H_4$; 8.10 ppm, s, $H_2$; 11.59 ppm, br., NH |
| 15 | $CDCl_3$ | = 35.1 ppm, $CH_3$; 122.1 ppm, $C_4$; 126.5 ppm, $C_5$; 136.9 ppm, $C_2$ | $CDCL_3$ | = 2.52 ppm, br., $BH_2$; 4.01 ppm, s, NMe; 7.25 ppm, s, $H_5$; 7.48 ppm, s; $H_4$; 8.35 ppm, s, $H_2$ |
| 16 | $(CD_3)_2CO$ | = 11.7 ppm, $CH_3$; 117.3 ppm, $C_4$; 126.5 ppm, $C_5$; 146.2 ppm, $C_2$ | $(CD_3)_2CO$ | = 2.50 ppm, br., $BH_2$; 2.63 ppm, s, $CH_3$; 7.18 ppm, d, $^3J_{H,H}$ = 1.6Hz, $H_5$; 7.38 ppm, d, $^3J_{H,H}$ = 1.62Hz, $H_4$; 12.15 ppm, br., NH |
| 18 | $CDCl_3$ | = 34.7 ppm, $NCH_3$; 47.8 ppm, $OCH_3$; 120.7 ppm, $C_4$; 126.9 ppm, $C_5$; 137.2 ppm, $C_2$ | $CDCl_3$ | = 2.65 ppm, br., $BH_2$; 3.53 ppm, s, $OCH_3$; 3.81 ppm, s, $NCH_3$; 7.00 ppm, s, $H_5$; 7.08 ppm, s, $H_4$; 7.99 ppm, s, $H_2$ |
| 19 | $CDCl_3$ | = 15.2 ppm, $CH_3$; 32.2 ppm, $NCH_2$; 34.8 ppm, $NCH_3$; 120.2 ppm, $C_4$; 127.1 ppm, $C_5$; 137.2 ppm, $C_2$ | $CDCl_3$ | = 1.10 ppm, t, $^3J_{H,H}$ = 7Hz, $CH_3$; 2.55 ppm, br., $BH_2$; 3.28 ppm, m, $^3J_{H,H}$ = 7Hz, $NCH_2$; 3.76 ppm, s, $NCH_3$; 5.68 ppm, br., NH, 6.89 ppm, s, $H_5$; 7.08 ppm, s, $H_4$; 8.24 ppm, s, $H_2$ |
| 20 | $CDCl_3$ | = 9.7 & 10.3 ppm, $CH_3$ s; 115.0 ppm & 134.2 ppm $C_4$ & $C_5$ respectively of 5-methyl derivative 122.2 ppm & 129.1 ppm; $C_5$ & $C_4$ of 4-methyl derivative; 134.3 ppm and 135.1 ppm, $C_2$, s | $CDCl_3$ | = 2.28 ppm, s & 2.31 ppm, s, $CH_3$, s; 2.41 ppm, br., $BH_2$ s; 6.78 ppm, s, $H_5$ of 4-methyl derivative; 6.84 ppm, s, $H_4$ of 5-methyl derivative; 7.74 ppm & 7.84 ppm, $H_2$, s |

[a] Carbon atom directly attached to boron was not observed.
[b] $^1H$ NMR of non-aromatic heterocyclic amine derivatives is second order in all cases. No attempts have been made to assign the peaks to axial and equitorial protons.
[c] In piperidine or substituted piperidine derivatives, the peaks due to $BH_2$ protons were obscured by the presence of other peaks in this region (1.5 to 2.0 ppm).

EXAMPLE X

Cytotoxic Activity

Boron derivatives of heterocyclic amines as prepared in the preceding Examples were tested for cytotoxicity activity by preparing a 1 mM solution of the drug in 0.05% tween 80/$H_2O$ by homogenization. The drug solutions were sterilized by passing them through an Acrodisc 45 μM. The following cell lines were maintained by the parenthetically identified literature technique: murine $L_{1210}$ lymphoid leukemia (Geran, R. I. et al, *Cancer Chemotherapy Reports*, 972, 3, 7-9); $P_{388}$ lymphocytic leukemia (same); human $Tmolt_3$ (Minowada, J. et al, *J. Nat. Cancer Int.*, 1972, 49, 891-895); acute lymphoblastic T cell leukemia colorectal adenocarcinoma SW480 (Leibovitz, A., et al, *Cancer Res.*, 1976, 36, 4562-4569); lung bronchogenic MB-9812 (Aaronson, S. A., et al *Expt. Cell Res.*, 1970, 61, 1-5); osteosarcoma TE418 (Smith, H. S., et al, *Intl. J. Cancer*, 1976, 17, 219-234); KB epidermoid nasopharynx (Geran, R. I. et al, ibid; Eagle, H., *Proc. Soc. Expt. Biol.* 1955, 89, 362-364); HeLa-$S^3$ suspended cervical carcinoma (Puck, T. T., et al, *J. Exp. Med.*, 1956, 103, 273-283); and glioma EH 118 MG (Nelson-Rees, W. A., et al, *Int. J. Cancer*, 1975, 16, 74-82).

The protocol used to assess cytotoxicity was that of Geran et al (ibid). Standards were determined in each cell line. Values were expressed for the drug's cytotoxicity as $ED_{50}$ in μg/ml, i.e., the concentration which inhibits 50% of the cell growth determined by the trypan blue exclusion technique. Solid tumor cytotoxicity was determined by the method of Huang et al (*J. Pharm. Sci.*, 1972, 61, 108-110). Ehrlich ascites carcinoma in vivo tumor screens were conducted in $CF_1$ male mice (~28 g) with test drugs at 20 mg/kg/day I.P. by the method of Piantadosi, et al (*J. Pharm. Sci.*, 1969, 58, 831).

Mode of Action Studies for Compounds 4 and 7

In this test, a number of heterocyclic amine-boranes were evaluated for their anti-neoplastic activity.

In vitro incorporation of labeled precursors into DNA, RNA and protein of $L_{1210}$ cells ($10^6$) was determined for 60 minutes by the method of Liao et al (*Molecular Pharmac.*, 1976, 12, 167–176). Drugs were present at 1, 2 and 3 times the concentration of their respective $ED_{50}$ values in the tissue culture cells. The reaction mixtures were inactivated with acid. The DNA acid-soluble precipitate was collected by vacuum suction on GF/F glass fiber discs which were washed with cold 10% perchloric acid containing 1% sodium pyrophosphate. Acid-insoluble precipitates from the RNA and protein experiments were collected on GF/B and Whatman #3 filters, respectively, and were washed with 10% trichloroacetic acid. The filter discs were dried, placed in Scintivers ® and counted in a Packard Scintillation Counter. The following enzymatic activities were determined in cells at multiples of the $ED_{50}$ values for each drug. DNA polymerase α activity was determined on a cytoplasmic fraction using the incubation medium of Swada et al, *Cancer Res.*, 1974, 34, 3341–3346), with [$^3$H-methyl]-dTTP (82.4 Ci/mmol). dCTP. dGTP and dATP. Incubation was for 60 minutes at 37° C. The acid insoluble precipitate was collected on glass fiber discs and counted. Messenger, ribosomal and transfer RNA polymerase enzymes were separated by ammonium fractionation and the mRNA polymerase, tRNA polymerase and rRNA polymerase activities were determined using $^3$H-UTP (23.2 Ci/mmol). The reaction medium was inactivated with 10% perchloric acid containing 1% NaP-P and the acid insoluble $^3$H-RNA was collected on nitrocellulose filters and counted.[29] Formate incorporation into purines for 40 minutes at 37° C. was determined by the method of Spassova et al.[30] with 0.5 mCi $^{14}$C-formic acid (52 mCi/mmol). Purines were separated by silica gel TLC eluted with n-butanol acetic acid:water (4:1:5). Using standards for guanine and adenine, the appropriate spots were scraped and counted. Inosinic acid dehydrogenase activity was determined by the method of Becker and Lohr (*Klin. Worchenschr.*, 979, 57, 1109–1115) using 30 minutes incubation at 37° C. with (8-$^{14}$C-) inosine-5'-monophosphate (61 mCi/mmol). XMP was separated from IMP by TLC on PEI plates eluted with 0.5M $(NH_4)_2SO_4$). The appropriate spot (standard, XMP) was scraped and counted. Thymidylate synthetase activity was determined in a cell supernatant (9000 g×10 minutes) fraction by the method of Kampf et al. *J. Med. Chem.*, 1966, 20, 4802–4809) with $^3$H-dUMP (11 Ci/mmol). The nucleotides were absorbed on charcoal, filtered on Whatman #1 filters and a sample of the aqueous filtrate was counted. N-Ethylmaleimide, a known thiol alkylating agent, from 0–200 nM concentration, was utilized to assess inhibition of the enzyme activities.

Ribonucleotide diphosphate reductase activity was measured by a modification of the method of Moore and Hurlbert *J. Boil. Chem.*, 1966, 20, 4802–4809). An aliquot of 5000×g supernatant was incubated for 30 minutes at 37° C. with reaction medium containing 0.1 mCi [5- $^3$H]-CDP (16.2 Ci/mmole). The reaction was stopped by boiling; samples were incubated with calf intestine alkaline phosphatase, spotted on PEI plates, and eluted with ethanol/saturated sodium borate/ammonium acetate/EDTA. Plates were scrapped at the $R_f$ of the standard, deoxycytidine, and counted. Deoxyribonucleotide triphosphates were extracted with perchloric acid by the method of Bagnara and Finch (*Anal. Biochem.*, 1972, 45, 24). After neutralization with 5N KOH and 1M $KH_2PO_4$ deoxyribonucleotide triphosphate levels were determined by the 723-727). The neutralized extract was incubated for 30 minutes at 37° C. with the reaction medium containing calf thymus DNA, *E. coli* DNA polymerase I, non-limiting amounts of three deoxyribonucleotide triphosphates not being assayed, including 0.04 mCi [$^3$H-methyl]-dTTP (80 Ci/mmole) or [5- $^3$H]-dCTP (15-30 Ci/mmole). The samples were spotted on Whatman #3 filters, which were rinsed in 5% trichloroacetic acid/40 nM sodium pyrosphate and in 95% ethanol, after which they were dried, and counted for radioactivity. Thymidine kinase, TMP kinase and TDP kinase activities were determined using $^3$H-thymidine incubated in the medium of Maley and Ochoa *J. Biol. Chem.*, 1958, 233, 1538–1543). After extraction with ether, the aqueous layer was plated on PEI-F plates and eluted with 0.5M formic acid: lithium chloride (1:1). The areas identical to the $R_f$ of the standards of thymidine, TMP and TDP were scraped and counted. DNA strand scission studies were conducted on $L_{1210}$ cells incubated with 10 mCi of methyl-$^3$H thymidine. 84.0 Ci/mmol for 24 hr at 3×X the $ED_{50}$ values for compound 4 or 7 using sucrose density gradients.

Results

Boron derivatives of saturated (piperidine and piperazine) and unsaturated (imidazole) amines demonstrated significant cytotoxicity against both murine and human neoplastic cell lines, as shown in Table 4 below.

Most of the compounds demonstrated marked activity against the growth of $L_{1210}$. $Tmolt_3$ and Hela-$S^3$. All unsaturated amine-borane derivatives (13–19) were also found to be active against the growth of lung bronchogenic tumor. Among saturated amine derivatives, only 4-methyl piperazine derivatives (11 and 12) showed significant activity in this screen and even in these cases, the activity was lower than that observed for the unsaturated amine derivatives. The data indicate that in heterocyclic amine-boranes, the unsaturation in the ring may be important for good biological activity against lung bronchogenic tumor. Growth of human osteosarcoma was significantly inhibited by compounds 1–4, 17 and 19. Compounds 8, 9, and 11 were active in the murine $P_{388}$ lymphocytic screen while compound 10 was marginally active. Compounds 1 and 17 were the only compounds which showed activity against human adenocarcinoma colorectal SW480 growth. Compounds 12, 16, 17 and 19 demonstrated good activity in the KB nasopharynx screen. All of the compounds except 1, 2, and 4 demonstrated activity against the growth of human glioma cells. A comparison of the activity of compounds 2, 3, 8, 14, 15 and 16 all of which have cyanoborane functionality, with that of compounds 4, 5, 6, 7, 9, 11 and 13 (with carboxyborane functionality) indicates that cyano or carboxy groups have little effect on activity. Compound 17 demonstrated the best profile with the most effective $ED_{50}$ value in most of the tumor lines with the exception of the $P_{388}$ cell line. The broad spectrum cytotoxicity of this compound may be associated with its high reactivity.

Select compounds were tested in the in vivo $P_{388}$ lymphocytic screen at 20 mg/kg/day I.P. Compounds 1, 4, 7, 8, 9 and 10 afforded T/C% −139, 122, 153,126, 135 and 149, respectively. All of the remaining compounds were less than T/C%−120 at this dose. In the in vivo Ehrlich ascites carcinoma screen at 20 mg/kg/day compound 8 resulted in 100% inhibition of growth; compound 18, 99%; compound 9 and 15, 83%; compound 11 and 16, 78%; compound 13, 73%; compound 17, 71%; compound 14, 66% and compound 4, 65%. All other compounds showed less than 60% inhibition. In vivo Lewis lung carcinoma activity was demonstrated for compounds 6, 9, 19, 11, 14, 16 and 18 with a T/C%−137, 141, 120, 179, 148, 163 and 152 at 8 mg/kg/day I.P. Compounds 3, 4 and 12 were inactive at this dose. Compounds 9, 12 and 15 were inactive in the $L_{1210}$ leukemia screen at 20 mg/kg/day. Compounds 4 and 14 afforded T/C%−123 and 125, respectively.

ity was moderately inhibited (20-29%). Examination of the deoxyribonucleotide pool levels at 3×the $ED_{50}$ values showed marked reduction of dGTP and dTTP i.e., >90%, dCTP levels were reduced >70% by 4 and 7 and dATP levels were lowered 26% by 4 and 63% by 7.

Kinetic studies of the inhibition of these enzyme activities at 3×the $ED_{50}$ values showed that thymidine kinase, TDP kinase, PRPP amidotransferase, IMP dehydrogenase and dihydrofolate reductase activities were inhibited with time over a 60 minute incubation period. The activity of TDP kinase was inhibited greater than 60% at 15 minutes. Thymidine kinase was inhibited ~40% by 15 minutes, whereas PRPP amidotransferase was inhibited > 25% at 15 minutes.

TABLE 4

| | $ED_{50}$ (µg/ml) Cytotoxicity | | | | | | | | |
|---|---|---|---|---|---|---|---|---|---|
| Compound Number | Human Lung Bronchogenic | Human lymphocyte Tmolt$_3$ | Human Osteo-Sarcoma | $L_{1210}$ Lymphoid Leukemia | Human HeLa-S$^3$ | $P_{388}$ Lymphocytic Leukemia | Human Colon SW480 | Human KB | Human Glioma |
| CYTOTOXICITY | | | | | | | | | |
| 1 | 6.03 | 3.53 | 3.31 | 3.75 | 2.24 | 4.49 | 3.99 | 6.31 | 8.36 |
| 2 | 5.41 | 2.85 | 2.97 | 3.83 | 2.35 | 4.49 | 6.32 | 7.74 | 4.93 |
| 3 | 6.02 | 1.08 | 3.64 | 3.67 | 2.56 | 9.93 | 7.21 | 7.42 | 3.98 |
| 4 | 6.90 | 1.74 | 2.53 | 1.74 | 1.92 | 5.62 | 4.21 | 6.89 | 4.96 |
| 5 | 7.12 | 3.10 | 4.41 | 3.34 | 1.60 | 10.23 | 6.19 | 7.23 | 2.14 |
| 6 | 6.30 | 1.96 | 6.65 | 4.44 | 2.14 | 12.30 | 7.02 | 7.12 | 2.44 |
| 7 | 5.99 | 2.83 | 6.04 | 2.68 | 2.46 | 11.91 | 6.54 | 6.65 | 3.22 |
| 8 | 5.37 | 1.63 | 6.24 | 4.06 | 2.30 | 3.64 | 6.22 | 6.39 | 2.57 |
| 9 | 4.96 | 2.83 | 7.06 | 3.56 | 1.23 | 2.93 | 5.32 | 6.54 | 2.23 |
| 10 | 4.75 | 2.34 | 6.65 | 2.62 | 2.92 | 4.00 | 7.41 | 5.62 | 2.36 |
| 11 | 3.51 | 2.61 | 7.47 | 2.85 | 1.71 | 3.89 | 6.50 | 6.19 | 2.53 |
| 12 | 3.72 | 4.19 | 6.26 | 3.00 | 2.03 | 4.87 | 6.63 | 2.18 | 1.67 |
| 13 | 2.78 | 2.72 | 7.17 | 2.46 | 1.97 | 9.66 | 4.43 | 4.43 | 3.04 |
| 14 | 2.92 | 2.93 | 4.09 | 5.12 | 1.92 | 4.83 | 4.16 | 6.15 | 3.22 |
| 15 | 2.66 | 2.39 | 6.86 | 3.12 | 2.40 | 5.13 | 6.77 | 7.18 | 3.00 |
| 16 | 3.09 | 0.65 | 6.48 | 3.56 | 1.44 | 4.47 | 4.66 | 2.18 | 2.06 |
| 17 | 1.28 | 2.17 | 1.92 | 1.78 | 2.46 | 4.88 | 1.69 | 1.85 | 0.472 |
| 18 | 1.76 | 1.08 | 6.89 | 3.69 | 3.47 | 5.63 | 4.06 | 6.54 | 1.715 |
| 19 | 3.36 | 1.79 | 2.53 | 1.80 | 2.24 | 6.00 | 7.76 | 2.52 | — |
| CYTOTOXICITY OF HETEROCYCLIC AMINE-BORANE DERIVATIVES | | | | | | | | | |
| 20 5FU | 5.64 | 2.14 | — | 1.41 | 2.47 | 3.72 | 3.09 | 1.25 | 1.28 |
| 21 araC | 4.60 | 2.67 | — | 2.76 | 2.13 | 4.06 | 3.42 | 2.54 | 1.88 |
| 22 Hydrourea | 7.33 | 3.18 | 7.57 | 2.67 | 1.96 | — | 4.76 | 5.29 | 2.27 |
| 23 Cycloleucine | 4.36 | 2.38 | 6.18 | 3.08 | 2.38 | — | 3.81 | 5.71 | 5.89 |

Compounds 4 and 7 inhibited DNA, RNA and protein synthesis of $L_{1210}$ lymphoid leukemic cells in a dose dependent manner at 1, 2 and 3×the $ED_{50}$ values, as shown in Table 5 below. DNA synthesis was inhibited by compounds 4 and 7 more effectively than RNA and protein synthesis. The inhibition of DNA synthesis was not due to inhibition of the activities of DNA polymerase α, thymidylate synthetase, carbamyl phosphate synthetase and aspartate amidotransferase. The purine de novo synthetic pathway was inhibited by both drugs at its regulatory sites, i.e., PRPP amidotransferase and IMP dehydrogenase. Furthermore, dihydrofolate reductase was significantly inhibited in a dose response manner by about 65%. Ribonucleotide reductase activ- Drugs 4 and 7 caused no changes in DNA viscosity or thermal denaturation at 3× the $ED_{50}$ values after inhibition for 24 hours at 37° C. Both drugs at 3×their $ED_{50}$ values appear to have caused strand scission with low molecular weight DNA which is indicative of topoisomerase II inhibition.

The mode of action of enzyme-inhibiting compounds as antineoplastic agents in the practice of the present invention comprises action of the compounds at multiple sites, including topoisomerase II as well as enzymes including PRPP amidotransferase, IMP dehydrogenase, dihydrofolate reductase, and ribonucleoside reductase.

TABLE 5

The effects of Compounds 4 and 7 on the Nucleic Acid and Protein Metabolism of $L_{1210}$ Lymphoid Leukemic Cells In Vitro

| | | Percent of Control | | | | | |
|---|---|---|---|---|---|---|---|
| | | Compound 4 - $ED_{50}$ Value | | | Compound 7 - $ED_{50}$ Value | | |
| Assay (N = 6) | Control | 1X | 2X | 3X | 1X | 2X | 3X |
| DNA Synthesis | 100 ± 6$^a$ | 67 ± 6* | 64 ± 5* | 29 ± 5* | 74 ± 5 | 69 ± 8* | 34 ± 5* |
| RNA Synthesis | 100 ± 4$^b$ | 93 ± 7 | 78 ± 7 | 67 ± 6* | 124 ± 7 | 99 ± 5 | 60 ± 5* |
| Protein Synthesis | 100 ± 6$^c$ | 91 ± 8 | 55 ± 5* | 52 ± 6* | 86 ± 6 | 76 ± 4 | 64 ± 4* |
| DNA Polymerase α | 100 ± 8$^d$ | — | — | 248 ± 9 | — | — | 205 ± 10 |
| mRNA Polymerase | 100 ± 9$^e$ | — | — | 551 ± 8 | — | — | 651 ± 12 |

TABLE 5-continued

The effects of Compounds 4 and 7 on the Nucleic Acid and Protein Metabolism of $L_{1210}$ Lymphoid Leukemic Cells In Vitro

| Assay (N = 6) | Control | Compound 4 - $ED_{50}$ Value | | | Compound 7 - $ED_{50}$ Value | | |
|---|---|---|---|---|---|---|---|
| | | 1X | 2X | 3X | 1X | 2X | 3X |
| rRNA Polymerase | 100 ± 6[f] | — | — | 214 ± 8 | — | — | 234 ± 10 |
| tRNA Polymerase | 100 ± 5[g] | — | — | 24 ± 3* | — | — | 22 ± 4* |
| Thymidine Kinase | 100 ± 6[h] | — | 93 ± 3 | 43 ± 4* | — | 63 ± 6* | 38 ± 5* |
| Thymidine Monophosphate Kinase | 100 ± 9[i] | — | — | 82 ± 7 | — | — | 94 ± 6 |
| Thymidine Diphosphate Kinase | 100 ± 6[j] | — | — | 10 ± 2* | — | — | 18 ± 3* |
| Thymidylate Synthetase | 100 ± 7[k] | — | — | 131 ± 10 | — | — | 108 ± 9 |
| Carbamoyl Phosphate Synthetase | 100 ± 8[l] | — | — | 116 ± 8 | — | — | 132 ± 11* |
| Aspartate Amido Transferase | 100 ± 6[m] | — | — | 111 ± 5 | — | — | 96 ± 7 |
| PRPP Amido Transferase | 100 ± 5[n] | — | 74 ± 6* | 16 ± 3* | — | 72 ± 6* | 30 ± 5* |
| IMP Dihydrogenase | 100 ± 7[o] | — | 123 ± 6 | 41 ± 4* | — | 88 ± 7 | 64 ± 5* |
| Dihydrofolate Reductase | 100 ± 6[p] | 94 ± 6 | 74 ± 5 | 31 ± 3* | 77 ± 6* | 66 ± 5* | 13 ± 3* |
| Ribonucleotide Reductase | 100 ± 7[q] | — | 123 ± 8 | 71 ± 7* | — | 88 ± 8 | 80 ± 7 |
| d(ATP) Levels | 100 ± 8[r] | — | — | 74 ± 6 | — | — | 37 ± 5 |
| d(GTP) Levels | 100 ± 5[s] | — | — | 2.5 ± 0.5 | — | — | 0.9 ± 0.6 |
| d(CTP) Levels | 100 ± 7[t] | — | — | 25 ± 4 | — | — | 27 ± 3 |
| d(TTP) Levels | 100 ± 7[u] | — | — | 3.2 ± 0.8 | — | — | 7.4 ± 2 |

*$p \leq 0.001$
[a] 26152 dpms/$10^6$ cells/60 min
[b] 4851 dpms/$10^6$ cells/60 min
[c] 7164 dpms/$10^6$ cells/60 min
[d] 47804 dpms $^3$H-dTTP incorporated/hr/mg of protein
[e] 1502 dpms 3H-UTP incorporated/hr/mg of protein
[f] 4239 dpms 3H-UTP incorporated/hr/mg of protein
[g] 6400 dpms 3H-UTP incorporated/hr/mg of protein
[h] 0.867 Δ O.D. 340/hr/mg of protein
[i] 0.625 Δ O.D. 340/hr/mg of protein
[j] 0.121 Δ O.D. 340/hr/mg of protein
[k] 18463 dpms $^3$H$_2$O formed/hr/$10^6$ cells
[l] 0.392 moles of citrulline formed/hr/mg of protein
[m] 1.064 moles of N-carbamyl aspartate formed/hr/mg of protein
[n] 0.936 Δ O.D. units/hr/μg of protein
[o] 76058 dpms $^3$H-XMP formed/hr/mg of protein
[p] 0.868 Δ O.D. units/hr/mg of protein
[q] 2744 dpm $^3$Hd-CDP formed/hr/mg of protein
[r] 6.17 pmoles dATP/$10^6$ cells
[s] 5.27 pmoles dGTP/$10^6$ cells
[t] 6.87 pmoles dTTP/$10^6$ cells
[u] 6.94 pmoles dTTP/$10^6$ cells From the studies of compounds 4 and 7 in $L_{1210}$ lymphoid leukemia cells, it can be concluded that the major effects of the piperidine-carboxyborane and N-methylmorpholine-carboxyborane were on DNA metabolism at multiple sites. The de novo purine pathway, dihydrofolate reductase, nucleoside and nucleotide kinase activities and DNA strand scission appear to be sites where the boron compounds function to afford DNA synthesis inhibition and tumor cell death. The inhibition of any one of these parameters would be sufficient to account for the observed DNA synthesis inhibitions by the boron compounds. Thus, the effects of the boron compounds apparently are additive, with regard to causing cell death. Since the compounds afford significant inhibition of nucleoside and nucleotide kinase activity at 15 minutes incubation, these sites of the boron compound's action may be the key factor in affording cell death. The inhibition of purine de novo synthesis as well as the nucleoside and nucleotide kinase activities would explain the lower levels of d(NTP)'s available for DNA incorporation. Again, it should be noted that d(GTP) levels are affected more by drug treatment than d(ATP) levels and d(TTP) is lower than d(CTP) levels. This may reflect a differential effect of the boron compounds on the individual nucleotide kinases. d(GTP) may be affected more because metabolically it is generated directly from XMP, the end product of IMP dehydrogenase, whereas d(ATP) levels may not be affected by boron compound treatment as severely because of salvage pathways of the nucleotides. Any one of these sites where the boron compounds have been shown to inhibit $L_{1210}$ cell metabolism is feasible as a potential mechanism of action of useful antineoplastic agents.

EXAMPLE XI

In this test, a number of heterocyclic amine-boranes were evaluated to determine their anti-hyperlipidemic activity in rodents.

Pharmacology

Hypolipidemic Screens in Normal Rodents: Heterocyclic amine borane derivatives were suspended in 1% carboxymethyl cellulose-H$_2$-O and administered I.P. to $CF_1$ male mice (~25 g) for 16 days or orally to Sprague Dawley male rats (~300 g) by an intubation needle for 14 days. On days 9 and 14 or 16, blood was obtained by tail vein bleeding, and the serum was separated by centrifugation for 3 minutes. The serum cholesterol levels were determined by modification of the Lieberman Burchard reaction. The triglyceride content was determined by a commercial kit (Biodynamic/bmc Triglyceride Kit).

Liver, Small Intestine and Fecal Lioid Extraction: In Sprague Dawley male rats (~300 g) that had been administered compounds 10 and 19 at 8 mg/kg/day orally for 14 days, the liver, aorta, small intestine and fecal materials (24 h collection) were removed and a 10% homogenate in 0.25M sucrose plus 0.001M ethylenedinitril-otetra-acetic acid was prepared. An aliquot (2 mL) of the homogenate was extracted by the methods of Folch et al (*J. Biol. Chem.*, 226, 497) and Bligh and Dyer (Can. *J. Biochem. Physiol.*, 37, 911)), and the amount (mg) of lipid was determined. The lipid was taken up in methylene chloride and the cholesterol levels, triglyceride levels, neutral lipid content, phospholipid content, and amount of protein were determined.

Serum Lipoprotein Fractions: Sprague Dawley male rats (~300 g) Were administered compounds 10 and 19 at 8 mg/kg/day orally for 14 days. On day 14, blood was collected from the abdominal vein. Serum was separated from whole blood by centrifugation at 3500 rpm. Aliquots (3 mL) were separated by density-gradient ultracentrifugation, according to the method of Havel et al (*Ann. Rev. Med.*, 33, 417) as modified for rat by Mookerjea et al (*Lipids*, 10, 34) into the chylomicrons, very low density lipoproteins, high density lipoproteins and low density lipoproteins. Each of the fractions was analyzed for cholesterol, triglyceride, neutral lipid, phospholipids, and protein levels.

Enzymatic Studies: In vitro enzymatic studies were carried out using 10% homogenates of CF male mouse liver prepared in 0.25M sucrose plus 0.001 EDTA (pH 7.2) with 25–100μM of compound 10 and 19. Acetyl coenzyme A synthetase and adenosine triphosphate-dependent citrate lyase activities were determined spectrophotometrically at 540 nm as the hydroxyamate of acetyl coenzyme A formed after 30 minutes at 37° C. Mitochondrial citrate exchange was determined by the procedure of Robinson et al. (J. Biol. Chem., 246, 5280) using 1$^{14}$C-labeled sodium bicarbonate (41 mCi mmol) incorporated into mitochondrial $^{14}$-C-labeled citrate, after isolating rat mitochondria (9000 g×10 minutes) from the homogenates. The exchanges of the $^{14}$C-labeled citrate were determined after incubating the mitochondrial fraction, which was loaded with labeled citrate and test drugs for 10 minutes. Then the radioactivity was measured in the mitochondrial and supernatant fractions and expressed as a percentage. Cholesterol-7α-hydroxylase activity was determined by the method of Shefer et al (*J. Lipid Res.*, 9, 328) using [1,2-$^3$H] cholesterol (60 mCi/mmol) and acyl CoA cholesterol acyl transferase activity was determined by the method of Balasubramaniam et al (*Eur. J. Biochem.*, 90, 377) using [1-$^{14}$Cholic acid (56.7 mCi/mmol). Cholesterol synthesis was measured using [1-$^{14}$C]acetate-CoA (56 mCi/mmol) and a postmitochondrial supernatant (9000 g×20 minutes) incubated for 60 minutes at 37° C. The digitonide derivative of cholesterol was isolated and counted. Neutral cholesterol ester hydrolase activity was determined using $^{14}$C-cholesteryl oleate (57.0 mCi/mmol) incubated for 60 minutes with the postmitochondrial supernatant (9000 g×20 minutes) as described by Hall et al. Acetyl coenzyme A carboxylase activity was measured by the method of Greenspan and Lowenstein. Initially, the enzyme had to be polymerized for 30 minutes at 37° C., and then the assay mixture containing solution [$^{14}$C]bicarbonate (41.0 mCi/mmol) was added and incubated for 30 minutes at 37° C. with the test drug. Sn-Glycerol-3-phosphate acyl transferase activity was determined with glycerol-3-phosphate [L-2-$^3$H(N)] (7.1 Ci/mmol) and the microsomal fraction of the liver homogenates. The reaction was terminated after 10 minutes and the lipids were extracted with chloroform:methanol (2:1) containing 1% concentrated HCl and counted. Phosphatidylate phosphohydrolase activity was measured as the inorganic phosphate released after 30 minutes by the method of Mavis et al (*J. Lipid. Res.*, 19, 467). The released inorganic phosphate after development with ascorbic acid and ammonium molybdate was determined at 820 nm. Protein content for the enzyme assays was determined by the technique of Lowry et al (*J. Biol. Chem.*, 193, 265).

RESULTS

All of the heterocyclic amine-boranes possess some ability to lower serum cholesterol level by 15% to 43% and serum triglyceride levels by 5% to 47%, as shown by Table 6 below. Compounds 6 and 10 lowered serum cholesterol levels 43% and 41% respectively. Serum triglyceride levels were lowered 40% by 4, 47% by 11, 43% by 17, and 41% by 19. Compounds 10 and 19 were selected for further indepth studies [see Table 7 below] because these tow compounds afforded the best activity considering both screens. Both of these derivatives lowered rat serum cholesterol levels by greater than 40% after 14 days. Serum triglyceride levels were reduced 48% by 10, but only 22% by 19 on day 14. Compound 10 also caused a 6% reduction of the total body weight increase over 14 days, whereas 19 had no effect on body weight increase. Daily food consumption was reduced 14% by Compound 10 but was reduced only 5% by Compound 19 in rats. Tissue lipids were altered by 10 and 19, e.g., triglycerides were reduced in the liver with elevation of neutral lipids (fatty acids mono and diglycerides). Compound 19 elevated hepatic phospholipid levels. Small intestinal total lipids and cholesterol levels were reduced by 19. The phospholipids were lowered significantly by 10 and 19. Aorta cholesterol, triglyceride and phospholipid levels were reduced but neutral lipids were elevated by both agents. Bile cholesterol levels were elevated after treatment with either drug and triglyceride levels were elevated by 19. Fecal total lipids and cholesterol levels were elevated by both agents. Fecal neutral lipids were elevated by 19 and phospholipids were elevated by 10 and 19. Fecal protein content was increased by 10 and 19.

The lipid content of the serum lipoprotein fractions (see Table 8 below) was modulated by 10 and 19. Cholesterol content was reduced in the VLDL and LDL fractions but elevated in the HDL fraction. Triglycerides and neutral lipids were reduced in the LDL by both agents. Neutral lipids were also reduced in the chylomicrons by both agents. Triglyceride levels were elevated in the HDL fraction by 19. Phospholipid content was reduced in the HDL and VLDL by both agents, and in the LDL by 19. The protein content was reduced in the LDL and VLDL by 19 and in the LDL by 10.

Hepatic enzymatic activities (see Table 9 below) were also modulated by compound 10 and 19, e.g., ATP dependent citrate lyase, acetyl CoA synthetase, HMG CoA reductase and acetyl CoA carboxylase were reduced in activity by both agents in a concentration dependent manner. Cholesterol-7α-hydroxylase and neutral cholesterol ester hydrolase activities were elevated by both agents in a concentration dependent manner. Acyl CoA cholesterol acyl transferase, and sn-glycerol-3-phosphate acyl transferase activities were unaffected by the presence of the agents. Phosphatidylate phosphohydrolase activity was inhibited significantly by Compound 19 but not by Compound 10. Acetyl CoA carboxylase activity was increased by Compound 19 at lower concentrations.

TABLE 6

The Hypolipidemic Activity of Heterocyclic Amine Boranes in CF₁ Male Mice, IP

| N = 6 Compound # | Dose Mg/kg/day | Percent of Control (X ± SD) | | |
|---|---|---|---|---|
| | | Serum Cholesterol | | Serum Tri-glycerides |
| | | Day 9 | Day 16 | Day 16 |
| 1 | 20 | 67 ± 6* | 64 ± 5* | 74 ± 9* |
| 2 | 5 | 81 ± 8 | 66 ± 3* | 70 ± 7* |
| 3 | 8 | 66 ± 5* | 66 ± 6* | 69 ± 5* |
| 4 | 5 | 82 ± 4 | 71 ± 5* | 60 ± 8* |
| 5 | 8 | 77 ± 7* | 74 ± 4* | 76 ± 5* |
| 6 | 8 | 63 ± 6* | 57 ± 5* | 84 ± 7 |
| 7 | 8 | 86 ± 7 | 71 ± 7* | 80 ± 8 |
| 8 | 5 | 84 ± 7 | 73 ± 8* | 95 ± 11 |
| 9 | 8 | 81 ± 6 | 73 ± 5* | 86 ± 7 |
| 10 | 8 | 75 ± 4* | 59 ± 4* | 73 ± 5* |
| 11 | 8 | 106 ± 7 | 85 ± 6 | 53 ± 4* |
| 12 | 5 | 92 ± 6 | 83 ± 4 | 76 ± 6* |
| 13 | 8 | 75 ± 7* | 66 ± 6* | 63 ± 6* |
| 14 | 8 | 78 ± 6* | 67 ± 5* | 67 ± 5* |
| 15 | 8 | 74 ± 7* | 71 ± 8* | 74 ± 6* |
| 16 | 8 | 89 ± 8 | 76 ± 6* | 68 ± 5* |
| 17 | 8 | 72 ± 7* | 68 ± 5* | 57 ± 5* |
| 18 | 8 | 72 ± 6* | 66 ± 6* | 92 ± 7 |
| 19 | 8 | 74 ± 7* | 63 ± 4* | 59 ± 6* |
| Clofibrate | 150 | 88 ± 7 | 86 ± 6 | 75 ± 5* |
| 1% CMC | control | 100 ± 7$^a$ | 199 ± 6$^b$ | 100 ± 6$^c$ |

$^a$125 mg %
$^b$128 mg %
$^c$137 mg %
*p ≤ 0.001

TABLE 7

The Effects of Heterocyclic Amine Borones on Sprague Dawley Male Rat Lipid Levels After 14 days at 8 mg/kd/day Orally

| | Percent of Control (x ± SD) | | | | |
|---|---|---|---|---|---|
| | Serum Cholesterol | | Serum Triglycerides | | Percent Body |
| Compound | Day 7 | Day 14 | Day 7 | Day 14 | Wt |
| 10 | 47 ± 5* | 49 ± 4* | 81 ± 7 | 52 ± 5* | 125 |
| 19 | 74 ± 6* | 58 ± 5* | 91 ± 6 | 78 ± 6* | 132 |
| Clofibrate | 89 ± 7 | 86 ± 5 | 83 ± 6 | 74 ± 7* | — |
| lovastadin | 85 ± 4 | 82 ± 5 | 91 ± 5 | 86 ± 7 | — |
| 1% CMC | 100 ± 5$^a$ | 100 ± 6$^b$ | 100 ± 6$^c$ | 100 ± 6$^d$ | 131 |

$^a$73 mg %
$^b$75 mg %
$^c$111 mg %
$^d$112 mg %

| | Tissue Lipids | Percent of Control (x ± SD) | | | | |
|---|---|---|---|---|---|---|
| Compound | mg Lipid Extracted | Cholesterol | Triglyceride | Neutral Lipids | Phosphate Lipids | Protein |
| Liver | | | | | | |
| 10 | 103 ± 5 | 97 ± 7 | 22 ± 3* | 132 ± 7* | 102 ± 6 | 124 ± 5* |
| 19 | 74 ± 6* | 85 ± 6 | 78 ± 5* | 115 ± 6 | 133 ± 6* | 109 ± 7 |
| Control | 100 ± 6$^a$ | 100 ± 7$^b$ | 100 ± 6$^c$ | 100 ± 7$^d$ | 100 ± 8$^e$ | 100 ± 5$^f$ |
| Small Intestine | | | | | | |
| 10 | 108 ± 7 | 93 ± 7 | 165 ± 6* | 102 ± 6 | 20 ± 2* | 119 ± 5 |
| 19 | 88 ± 8 | 80 ± 6* | 95 ± 5 | 104 ± 4 | 41 ± 4* | 102 ± 6 |
| Control | 100 ± 7$^g$ | 100 ± 5$^h$ | 100 ± 8$^i$ | 100 ± 6$^j$ | 100 ± 5$^k$ | 100 ± 5$^l$ |
| Aorta | | | | | | |
| 10 | 115 ± 7 | 84 ± 6 | 81 ± 6* | 153 ± 5* | 75 ± 5* | 105 ± 6 |
| 19 | 117 ± 7 | 73 ± 5* | 83 ± 5 | 256 ± 6* | 81 ± 4 | 93 ± 5 |
| Control | 100 ± 5$^m$ | 100 ± 6$^n$ | 100 ± 5$^o$ | 100 ± 6$^p$ | 100 ± 5$^q$ | 100 ± 6$^r$ |
| Bile | | | | | | |
| 10 | — | 201 ± 12 | 106 ± 5 | 118 ± 6 | 104 ± 9 | 125 ± 6 |
| 19 | — | 156 ± 10 | 121 ± 5* | 104 ± 7 | 95 ± 8 | 111 ± 5 |
| Control | — | 100 ± 6$^s$ | 100 ± 6$^t$ | 100 ± 4$^u$ | 100 ± 5$^v$ | 103 ± 5$^w$ |
| Feces | | | | | | |
| 10 | 296 ± 10* | 239 ± 12* | 85 ± 6 | 97 ± 8 | 255 ± 6 | 205 ± 9* |
| 19 | 130 ± 8* | 176 ± 8* | 63 ± 7* | 127 ± 9 | 207 ± 3* | 201 ± 8* |

TABLE 7-continued

The Effects of Heterocyclic Amine Borones on Sprague Dawley Male Rat Lipid Levels After 14 days at 8 mg/kd/day Orally

| Control | | | | | | |
|---|---|---|---|---|---|---|
| | 100 ± 8$^x$ | 100 ± 5$^y$ | 100 ± 6$^z$ | 100 ± 8$^{aa}$ | 100 ± 5$^{bb}$ | 100 ± 5$^{cc}$ |

$^a$50.5 mg lipid/gm wet tissue
$^b$9.18 mg cholesterol/gm wet tissue
$^c$6.37 mg triglyceride/gm wet tissue
$^d$15.70 mg neutral lipid/gm wet tissue
$^e$27.19 mg phospholipid/gm wet tissue
$^f$12.02 mg/protein/gm wet tissue
$^g$68.20 mg lipid/gm wet tissue
$^h$12.02 mg cholesterol/gm wet tissue
$^i$11.20 mg triglyceride/gm wet tissue
$^j$16.98 mg neutral lipid/gm wet tissue
$^k$20.06 mg phospholipid/gm wet tissue
$^l$42.0 mg protein/gm wet tissue
$^m$67.5 mg lipid/gm wet tissue
$^n$5.77 mg/cholesterol/gm wet tissue
$^o$9.85 mg triglyceride/gm wet tissue
$^p$15.28 mg neutral lipid/gm wet tissue
$^q$28.8 mg phospholipid/gm wet tissue
$^r$11.71 mg protein/gm wet tissue
$^s$118 mg %
$^t$5 mg/mL
$^u$170 mg/ml
$^v$1.75 mg/ml
$^w$3.34 mg %
$^x$11.58 mg of lipid/gm wet tissue
$^y$2.84 mg cholesterol/gm wet tissue
$^z$1.86 mg trigylceride/gm wet tissue
$^{aa}$3.39 mg neutral lipid/gm wet tissue
$^{bb}$5.70 mg/phospholipid/gm wet tissue
$^{cc}$6.99 protein/gm wet tissue

TABLE 8

The Effects of Heterocyclic Amine Boranes on Serum Lipoprotein Fractions of Sprague Dawley Rats after 14 days, Orally

| | Percent of Control (x ± SD) | | | | |
|---|---|---|---|---|---|
| N = 6 | Cholesterol | Triglyceride | Neutral Lipids | Phospho-lipids | Protein |
| Chylomicron | | | | | |
| 10 | 98 ± 7 | 116 ± 8 | 75 ± 4* | 22 ± 7 | 103 ± 5 |
| 19 | 120 ± 7 | 95 ± 7 | 66 ± 6* | 11 ± 8 | 100 ± 6 |
| 1% CMC | 100 ± 6$^a$ | 100 ± 6$^b$ | 100 ± 6$^c$ | 100 ± 9$^d$ | 100 ± 6$^e$ |
| VLDL | | | | | |
| 10 | 39 ± 4* | 93 ± 7 | 92 ± 8 | 56 ± 6* | 98 ± 7 |
| 19 | 41 ± 3* | 90 ± 6 | 89 ± 7 | 88 ± 5 | 69 ± 6 |
| 1% CMC | 100 ± 6$^f$ | 100 ± 7$^g$ | 100 ± 7$^h$ | 100 ± 6$^i$ | 100 ± 6$^j$ |
| LDL | | | | | |
| 10 | 28 ± 3* | 48 ± 5* | 62 ± 5* | 124 ± 6* | 81 ± 6* |
| 19 | 36 ± 2* | 50 ± 4* | 53 ± 5* | 73 ± 4* | 45 ± 3* |
| 1% CMC | 100 ± 5$^k$ | 100 ± 7$^l$ | 100 ± 7$^m$ | 100 ± 5$^n$ | 100 ± 5$^o$ |
| HDL | | | | | |
| 10 | 209 ± 10* | 104 ± 5 | 97 ± 6 | 58 ± 5* | 89 ± 7 |
| 19 | 326 ± 12* | 165 ± 6* | 101 ± 6 | 65 ± 4* | 92 ± 8 |
| 1% CMC | 100 ± 7$^p$ | 100 ± 5$^q$ | 100 ± 7$^r$ | 100 ± 7$^s$ | 100 ± 7$^t$ |

$^a$337 μg cholesterol/ml serum
$^b$420 μg triglyceride/ml serum
$^c$67 μg neutral lipid/ml serum
$^d$149 μg phospholipid/ml serum
$^e$184 μg protein/ml serum
$^f$190 μg cholesterol/ml serum
$^g$22 μg triglyceride/ml serum
$^h$98 μg neutral lipid/ml serum
$^i$26 μg phospholipid/ml serum
$^j$50 μg protein/ml serum
*p ≤ 0.001
$^k$210 μg cholesterol/ml serum
$^l$45 μg triglyceride/ml serum
$^m$10 μg neutral lipid/ml serum
$^n$41 μg phospholipid/ml serum
$^o$122 μg protein/ml serum
$^p$544 μg cholesterol/ml serum
$^q$544 μg cholesterol/ml serum
$^r$620 μg neutral lipid/ml serum
$^s$153 μg phospholipid/ml serum
$^t$657 μg/ml serum

TABLE 9

The In Vitro Effects of Heterocyclic Amine Boranes on CF₁ Hepatic Liver De Novo Lipid Metabolic Enzymes Percent of Control (x ± SD)

| N = 6 Enzyme Assay | Control | Compound 10 25 μM | Compound 10 50 μM | Compound 10 100 μM | Compound 19 25 μM | Compound 19 50 μM | Compound 19 100 μM |
|---|---|---|---|---|---|---|---|
| Mitochondrail Citrate Lyase | 100 ± 5$^a$ | 100 ± 7 | 98 ± 6 | 77 ± 5* | 118 ± 9 | 119 ± 7 | 132 ± 10 |
| ATP Dependent Citrate Lyase | 100 ± 6$^b$ | 59 ± 4* | 26 ± 3 | 14 ± 3* | 30 ± 2* | 24 ± 3* | 22 ± 3 |
| Acetyl CoA Synthetase | 100 ± 6$^c$ | 80 ± 5* | 73 ± 5* | 47 ± 5* | 101 ± 5* | 85 ± 6 | 79 ± 52 |
| HMG CoA Reductase | 100 ± 7$^d$ | 77 ± 4* | 70 ± 5* | 67 ± 4* | 66 ± 5* | 61 ± 4* | 22 ± 3* |
| Cholesterol 7α Hydroxylase | 100 ± 7$^e$ | 102 ± 5 | 117 ± 9 | 121 ± 6* | 112 ± 7 | 123 ± 6* | 128 ± 5* |
| Acyl CoA Cholesterol Acyl Transferase | 100 ± 6$^f$ | 128 ± 7* | 96 ± 5 | 82 ± 5* | 126 ± 6 | 101 ± 6 | 93 ± 7 |
| Neutral Cholesterol Ester Hydrolase | 100 ± 8$^g$ | 153 ± 8* | 296 ± 12* | 338 ± 10* | 141 ± 8* | 184 ± 8* | 424 ± 9* |
| Acetyl CoA Carboxylase | 100 ± 5$^h$ | 102 ± 6 | 52 ± 4* | 45 ± 4* | 123 ± 9 | 121 ± 7 | 73 ± 5 |
| SN Glycerol 3 Phosphate Acyl Transferase | 100 ± 6$^i$ | 103 ± 7 | 105 ± 6 | 111 ± 6 | 100 ± 7 | 99 ± 8 | 97 ± 6 |
| Phosphatidylate Phosphohydrolase | 100 ± 8$^j$ | 112 ± 5 | 99 ± 7 | 90 ± 7 | 60 ± 5* | 53 ± 6* | 47 ± 4* |

$^a$30.8% exchange of mitrochondrial citrate
$^b$30.5 mg citrate hydrolyzed/gm wet tissue
$^c$28.5 mg acetyl CoA formed/gm wet tissue
$^d$384,900 dpm cholesterol formed/gm wet tissue
$^e$4808 dpm/mg of microsomal protein
$^f$224,000 dpm/mg microsomal protein
$^g$56,436 dpm/mg wet tissue
$^h$537,800 dpm/mg wet tissue
$^i$302010 dpm/mg wet tissue
$^j$16.7 μg Pi released/gm wet tissue

DISCUSSION

The cyano-, carboxy-, carbomethoxy-and carbamoyl-borane adducts of heterocyclic amines demonstrated potent hypolipidemic activity in rodents at 8 mg/kg/day. The saturated piperidine, piperazine and morpholine amine derivatives were in general equally active as the unsaturated imidazole derivatives. The cyanoboranes were approximately identical in activity as the carboxyborane derivatives. Compound 10, a 4-phenyl piperidine-carbomethoxy-borane, compound 17, trimethylamine-imidazolecarbonyldihydroboron, and Compound 19, 1-methyl imidazole-(N-ethyl) carbamoylborane, all afforded improved activity in both hypolipidemic screens. Compound 17 was not investigated further since it was suspected that in an aqueous medium it dissociated into imidazole and trimethyl amine carboxyborane. The latter compound possesses potent hypolipidemic activity in rodents.

Compounds 10 and 19 demonstrated the serum lipids were reduced in rats after oral administration at the low dose of 8 mg/kg/day and that they were more effective than the commercial agents clofibrate and lovastatin at their respective therapeutic doses of 150 mg/kg/day and 8 mg/kg/day.

The lipids removed from the serum compartment were not placed back into the tissues, but rather they appeared to be excreted into the bile and eliminated from the body via the feces. An additional mode of action of these agents appears to be the suppression of the rate limiting enzyme activities of de novo lipid synthesis. Suppression of ATP dependent citrate lyase and cytoplasmic acetyl CoA synthetase would lead to reduced levels of cytoplasmic acetyl CoA available for fatty acid and cholesterol synthesis. Furthermore, the rate limiting enzyme for cholesterol synthesis, HMG CoA reductase was significantly reduced by the heterocyclic amine-borane derivatives. The increase in cholesterol-7α-hydroxylase activity afforded by the agents suggests that more cholesterol would be converted to bile acids and the increase in neutral cholesterol ester hydrolase activity suggests more cholesterol esters would be broken down to free cholesterol for biliary excretion. Suppression of acetyl CoA carboxylase activity by the agents would lower fatty acid synthesis and suppression of phosphatidylate phosphohydrolase activity by 19 would lower the synthesis of triglycerides in the liver.

The most important finding of this study was that the heterocyclic amine-boranes modulated rat serum lipoproteins lipid levels. Both agents successfully lowered cholesterol levels of LDL and VLDL and elevated HDL cholesterol levels. Modulation of the cholesterol levels in these lipoproteins is desirable for a successful chemotherapy for atherosclerosis and hyperlipidemic disease states. AS atherosclerosis develops, LDL cholesterol levels are increased and HDL cholesterol levels are decreased resulting in more cholesterol being deposited in aorta plaques with the accumulation of cholesterol esters. Chemotherapy should reverse this process and the heterocyclic amine-borane derivatives significantly modulate the lipoprotein cholesterol ratio and accelerate the breakdown of cholesterol esters to cholesterol to bind the HDL. Modulation of the lipoprotein ratio in this direction is believed to protect humans from myocardial infarction. Most of the commercially available agents do not elevate HDL cholesterol by a large magnitude, e.g., clofibrate 4–16%, nicotinic acid 23%, benzafibrate 15%, fenofibrate 9–11%, and CS-514 14%, but other agents, e.g., probucal and d thyroxine, have no effect on HDL cholesterol levels.

EXAMPLE XII

Inhibition of the enzyme DNA topoisomerase II ("topo II") is determined by exposing known concentrations of sample compound (typically 100–200 μM) to reaction mixtures containing the topo II enzyme (HeLa "A") and knotted DNA. Knotted DNA is prepared as described in L. F. Liu, J. L. Davis, and R. Calendar, Nucleic Acids Research, 1981, 9(16), 3979–3989. Inhibition is noted when the ability of topo II to "unknot" the knotted DNA is reduced. On an agarose electrophoresis gel the DNA will appear smeared, as opposed to unknotted DNA which separates into distinct bands. Reaction mix is made to contain the following ingredients at the following concentrations: 0.05M Tris (pH 7.5), 0.1M KCl, 0.01M MgCl₂, 30 μg/ml BSA, 0.5 mM EDTA, 1.0 mM DTT, 1.0 mM ATP. In our experiments a "4×Reaction Mix" was used, meaning the ingredients were four times as concentrated as the previously described mix. To prepare samples a premix is made containing 2.5 µl "4×RM" per sample, 0.25 µl knotted DNA/sample, and enough water to bring the volume of each sample up to 8.0 µl. To each sample reaction 1.0 µl sample compound (at desired concentration) and 1.0 µl topoisomerase II is added so that the final volume of each sample reaction is 10 µl. The samples are allowed to react for one hour, at which time 2.5 µl of a Stop & Loading Buffer is added (50% w/v sucrose, 0.5% w/v SDS, 0.25% w/v BPB, & 0.25% XC) to stop the DNA-/enzyme reaction. Each sample, along with an enzyme and DNA control sample, is run overnight on an agarose electrophoresis gel at 23v. VP-16 (etoposide) is used as an internal standard for topo II inhibitors. The amine-boranes were found to be active at 100 µM concentrations. Data are shown in Table 10 below.

TABLE 10

| Topoisomerase II Inhibiting Activity of Amine-boranes | |
|---|---|
| Compound | Inhibitory Concentration (µM) |
| CH₃—⬡—NHBH₂COOCH₃ | 100 |
| C₆H₅—⬡—NHBH₂COOH | 100 |
| ⬡—NHBH₂COOH | 100 |
| CH₃—⬡—NHBH₂COOH | 100 |
| HN⬡NHBH₂COOH | 100 |
| O⬡NHBH₂COOH | 100 |
| O⬡NMeBH₂COOH | 100 |
| CH₃—N⬡NBH₂COOH | 100 |

EXAMPLE XIII

Anti-inflammatory Activity of Heterocyclic Amine-Boron Adducts $CF_1$ male mice (~25 g) were administered test drugs at 8 mg/kg in 0.0% Tween ® 80-$H_2O$ intraperitoneally 3 hours and again 30 minutes prior to the injection of 0.2 ml of 1% carrageenan in 0.9% saline into the plantar surface of the right hind foot. Saline was injected into the left hind foot which serves as a base line. After 3 hours, both feet were excised at the tibiotarsal (ankle)s joint according to the modified method of Winter (Winter et al., *Proc. Soc. Exp. Biol. Med.* 1962, 111, 544–547, and Hendershot and Forsaith, *J. Pharmacol. Exp. Ther.* 1970, 175 435–442). The control mice afforded a 78±3 mg increase in the paw weight. Data are presented in Table 11 below.

TABLE 11

| Compound No. (reference to Table 1 Nos.) | $CF_1$ Mice % of Control (20 mg/kg × 2) | Sprague Dawley Rats Antiarthritic (2.5 mg/kg/day) |
|---|---|---|
| 1 | 55 | 15 |
| 2 | 77 | 80 |
| 3 | 83 | — |
| 4 | 74 | 53 |
| 5 | 79 | |
| 6 | 66 | |
| 7 | 67 | |
| 8 | 91 | |
| 9 | 80 | |
| 10 | 67 | |
| 11 | 80 | |
| 12 | — | |
| 13 | — | |
| 14 | 99 | |
| 15 | 71 | |
| 16 | 62 | |
| 17 | 86 | |
| 18 | 76 | |
| 19 | 70 | |

While the invention has been described herein with reference to illustrated compounds and specific embodiments of the invention, it will be appreciated that numerous variations, modifications, and other embodiments are possible, and accordingly, all such variations, modifications, and embodiments are to be regarded as being within the spirit and scope of the invention.

What is claimed is:

1. A heterocyclic amine-borane of the formula:

$$A - \underset{\underset{R_1}{|}}{\overset{\overset{H}{|}}{B}} - R_2$$

wherein:

A is a heterocyclic amine moiety (i) attached to the boron atom by a nitrogenboron coordinate bond, (ii) selected from the group consisting of piperidine, piperazine, imidazole, pyradole, pyrazine, pyrrole, pyrrolidine, indole, indoline, quinoline, isoquinoline, thiazole, oxazole, and thiazolidine, and (iii) wherein the heterocyclic amine moiety is optionally substituted with one or more substituents selected from the group consisting of nitro, halo, thiol, hydroxy, $C_1$-$C_{10}$ alkoxy, $C_1$-$C_{10}$ alkyl, phenyl, $C_1$-$C_{10}$ alkylphenyl, phenyl $C_1$-$C_{10}$ alkyl;

$R_1$ is selected from H, $C_1$-$C_{10}$ alkylphenyl, and phenyl $C_1$-$C_{10}$ alkyl, and $R_2$ is selected from COOH, $COOR_3$, and $CONHR_3$ where $R_3$ is selected from H, $C_1$-$C_{10}$ alkyl, phenyl, $C_1$-$C_{10}$ alkylphenyl, and phenyl $C_1$-$C_{10}$ alkyl.

2. A heterocyclic amine-borane compound according to claim 1, wherein $R_1$ is H or $C_1$-$C_{10}$ alkyl.

3. A heterocyclic amine-borane compound according to claim 1, wherein $R_3$ is $C_1$-$C_{10}$ alkyl.

4. A heterocyclic amine-borane compound according to claim 1, wherein A is selected from the group consisting of piperdine, piperazine, and imidazole, and substituted forms thereof.

5. A heterocyclic amine-borane compound according to claim 1, substituted with one or more substituents selected from the group consisting of nitro, $C_1$–$C_{10}$ alkoxy, hydroxy, thiol, and halo.

6. A heterocyclic amine-borane compound according to claim 1, substituted with one or more substituents selected from the group consisting of $C_1$–$C_{10}$ alkyl, phenyl, $C_1$–$C_{10}$ alkylphenyl, and phenyl $C_1$–$C_{10}$ alkyl.

7. A heterocyclic amine-borane compound selected from the group consisting of:
   a. 1-Methylimidazole3-carboxyborane
   b. 1-Methylimidazole-3-carbomethoxyborane
   c. 1-Methylimidazole-3-(N-ethylcarbamoyl)borane
   d. 1-Methylimidazole-3-carboethoxyborane
   e. 1,2-Dimethylimidazole-3-carboxyborane
   f. Imidazole-3-carboxyborane
   g. 4-Methylimidazole-3-carboxyborane
   g. Piperazine-1-carboxyborane
   h. 1-Methylpiperazine-1-carboxyborane
   i. 2-methylpiperazine-1-carboethoxyborane
   j. Piperidine-1-(N-ethylcarbamoyl)borane
   k. 2-Methylpiperidine-1-carboethoxyborane
   l. 4-Methylpiperidine-1-carbomethoxyborane
   m. 4-Phenylpiperidine-1-carboxyborane
   n. 4-Benzylpiperidine-1-carboxyborane
   o. 4-Hydroxypiperidine-carbomethoxyborane
   p. Pyrazine-1-carboxyborane
   q. Pyrrole-1-carbomethoxyborane
   r. Pyrrolidine-1-carbomethoxyborane
   s. 8-Methylquinoline-1-carboxyborane
   t. Thiazole-3-carboxyborane.

8. A heterocyclic amine-borane compound selected from the group consisting of:

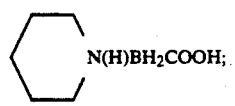

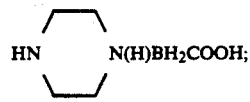

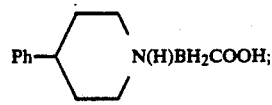

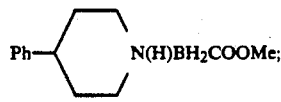

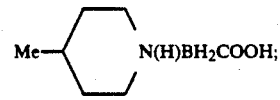

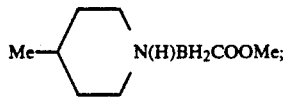

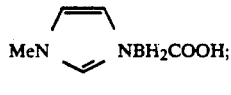

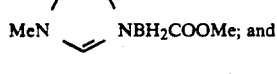

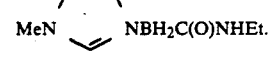

* * * * *